United States Patent
Jakob-Roetne et al.

(10) Patent No.: US 9,714,239 B2
(45) Date of Patent: Jul. 25, 2017

(54) N-PHENYL-LACTAM DERIVATIVES CAPABLE OF STIMULATING NEUROGENESIS AND THEIR USE IN THE TREATMENT OF NEUROLOGICAL DISORDERS

(71) Applicant: Hoffmann-La Roche Inc., Little Falls, NJ (US)

(72) Inventors: Roland Jakob-Roetne, Inzlingen (DE); Juergen Wichmann, Steinen (DE); Jens-Uwe Peters, Grenzach-Whylen (DE); Ravi Jagasia, Loerrach (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/213,622

(22) Filed: Jul. 19, 2016

(65) Prior Publication Data

US 2016/0326150 A1 Nov. 10, 2016

Related U.S. Application Data

(63) Continuation of application No. PCT/EP2015/050521, filed on Jan. 14, 2015.

(30) Foreign Application Priority Data

Jan. 20, 2014 (EP) .................................. 14151754

(51) Int. Cl.
| | |
|---|---|
| *C07D 413/10* | (2006.01) |
| *C07D 401/10* | (2006.01) |
| *C07D 403/10* | (2006.01) |
| *C07D 401/14* | (2006.01) |

(52) U.S. Cl.
CPC ......... *C07D 413/10* (2013.01); *C07D 401/10* (2013.01); *C07D 401/14* (2013.01); *C07D 403/10* (2013.01)

(58) Field of Classification Search
CPC .. C07D 401/10; C07D 401/14; C07D 403/10; C07D 413/10
See application file for complete search history.

(56) References Cited

FOREIGN PATENT DOCUMENTS

| EP | 2 455 370 A1 | 5/2012 | |
| EP | 2455370 | * 5/2012 | ........... C07D 233/61 |
| WO | 2005/090300 A1 | 9/2005 | |

* cited by examiner

*Primary Examiner* — Erich A Leeser

(57) ABSTRACT

The present invention relates to compounds of the general formula I wherein Het, $R^1$, $R^2$, W and X are as defined herein. Compounds of formula I are useful for treating neuropsychiatric disorders.

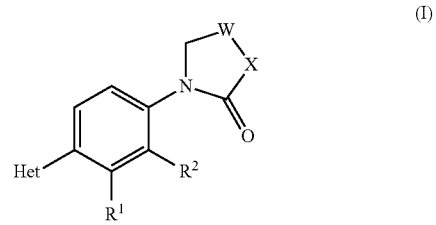

10 Claims, No Drawings

N-PHENYL-LACTAM DERIVATIVES CAPABLE OF STIMULATING NEUROGENESIS AND THEIR USE IN THE TREATMENT OF NEUROLOGICAL DISORDERS

CROSS REFERENCE TO RELATED APPLICATIONS

This application is a continuation of International Application No. PCT/EP2015/050521 having an international filing date of Jan. 14, 2015 and which claims benefit under 35 U.S.C. §119 to European Patent Application No. 14151754.0 filed Jan. 20, 2014. The entire contents of both are incorporated herein by reference.

FIELD OF THE INVENTION

The present invention relates to novel compounds of formula I, wherein $R^1$, $R^2$, Het, W and X are as described herein, having pharmaceutical activity, their manufacture, pharmaceutical compositions containing them and their potential use as medicaments.

BACKGROUND OF THE INVENTION

Neurogenesis occurs in the developing and adult brain. Conceptually, this process of neurogenesis can be divided into four steps: (i) proliferation of NSCs; (ii) neuronal fate determination of NSC; (iii) survival and maturation of new neurons; and (iv) functional integration of new neurons into the neuronal network.

Adult neurogenesis is a developmental process that occurs throughout live in the adult brain whereby new functional neurons are generated from adult neural stem cells. Constitutive adult neurogenesis under physiological conditions occurs mainly in two "neurogenic" brain regions, 1) the sub-granular zone (SGZ) in the dentate gyrus of the hippocampus, where new dentate granule cells are generated, 2) the sub-ventricular zone (SVZ) of the lateral ventricles, where new neurons are generated and then migrate through the rostral migratory stream (RMS) to the olfactory bulb to become interneurons.

Extensive evidence suggests that hippocampal adult neurogenesis plays an important role in cognitive and emotional states albeit the precise function remains elusive. It has been argued that the relatively small number of newborn granule neurons can affect global brain function because they innervate many interneurons within the dentate gyrus, each of which inhibits hundreds of mature granule cells leading to a neurogenesis-dependent feedback inhibition. In combination with a low threshold for firing the newborn neurons trigger responses to very subtle changes in context. Disturbances in this process may manifest behaviorally in deficits in pattern separation related to psychiatric diseases. For example, adult hippocampal neurogenesis correlates with cognitive and emotional capacity, e.g. physical exercise, exposure to an enriched environment and typical antidepressants concomitantly promote adult hippocampal neurogenesis and cognition and/or emotional states, while chronic stress, depression, sleep deprivation and aging decrease adult neurogenesis and associate with negative cognitive and/or emotional states (Neuron 70, May 26, 2011, pp 582-588 and pp 687-702; WO 2008/046072). Interestingly, antidepressants promote hippocampal adult neurogenesis and their effects on certain behaviors require the stimulation of neurogenesis. Neurogenesis in other adult CNS regions is generally believed to be very limited under normal physiological conditions, but could be induced after injury such as stroke, and central and peripheral brain damage.

It is therefore believed that stimulation of adult neurogenesis represents a neuro-regenerative therapeutic target for normal aging and in particular for a variety of neurodegenerative and neuropsychiatric diseases, including schizophrenia, obsessive-compulsive personality disorder, major depression, bipolar disorders, anxiety disorders, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss (Neuroscience, 167 (2010) 1216-1226; Nature Medicine, Vol. 11, number 3, (2005), 271-276) tinnitus, spinocerebellar ataxia, amyotrophic lateral sclerosis, multiple sclerosis, Huntington's disease, stroke, and disturbances due to radiation therapy, chronic stress, or abuse of neuro-active drugs, such as alcohol, opiates, methamphetamine, phencyclidine and cocaine (US 2012/0022096).

The stimulation of adult neurogenesis represents also a therapeutic target for optic neuropathy (S. Isenmann, A. Kretz, A. Cellerino, Progress in Retinal and Eye Research, 22, (2003) 483) and macular degeneration (G. Landa, O. Butovsky, J. Shoshani, M. Schwartz, A. Pollack, Current Eye Research 33, (2008) 1011).

Hence, chemical stimulation of adult neurogenesis offers new regenerative avenues and opportunities to develop novel drugs for treating neurological diseases and neuropsychiatric disorders.

BRIEF SUMMARY OF THE INVENTION

The present invention relates to compounds of the general formula

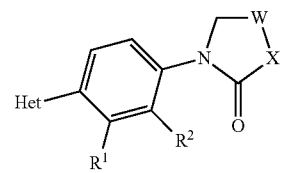

wherein
Het is oxazole-5-yl, pyridin-4-yl, or pyrazol-4-yl;
$R^1$ and $R^2$ are each independently hydrogen, lower alkyl, lower alkoxy, or halogen;
W is —$CH_2$— or —$CH_2CH_2$—;
X is $CR^3R^4$ or $NR^5$;
$R^3$ is hydrogen or lower alkyl;
$R^4$ is —$(CH_2)_n$-phenyl, optionally substituted by halogen, lower alkoxy, lower alkyl substituted by halogen, lower alkoxy substituted by halogen or lower alkyl;
$R^5$ is CHR-phenyl or $CH_2$CHR-phenyl, optionally substituted by halogen, lower alkoxy, lower alkyl substituted by halogen, lower alkoxy substituted by halogen or lower alkyl, or is CHR-pyridin-2-yl, CHR-pyridin-3-yl or CHR-pyridin-4-yl;
R is hydrogen or lower alkyl;
n is 0 or 1;

or to a pharmaceutically acceptable acid addition salt, to a racemic mixture or to its corresponding enantiomer and/or optical isomer thereof.

Another object of the present invention is to provide compounds and compositions containing said compounds that modulate neurogenesis any may therefore be used for the treatment of schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine.

Yet another object of the present invention provide process to prepare compounds of formula I.

DETAILED DESCRIPTION OF THE INVENTION

The present invention relates to compounds of formula I and to their pharmaceutically acceptable salts, in cases where this applies to mixtures of enantiomers or diastereomers or their enantiomerically or diastereomerically pure forms, or mixtures of their enantiomerically or diastereomerically pure forms. The present invention further relates to these compounds as pharmaceutically active substances, to the processes for their production, as well as to the use in the treatment or prevention of disorders, relating to neurogenesis, schizophrenia, obsessive-compulsive personality disorder, depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, mild cognitive impairment, chemotherapy-induced cognitive dysfunction ("chemobrain"), Down syndrome, autism spectrum disorders, hearing loss, tinnitus, spinocerebellar ataxia, amyotrophic lateral sclerosis, multiple sclerosis, Huntington's disease, stroke, and disturbances due to radiation therapy, chronic stress, optic neuropathy or macular degeneration, or abuse of neuro-active drugs, such as alcohol, opiates, methamphetamine, phencyclidine or cocaine.

The most preferred indications for compounds of formula I are Alzheimer's disease, depression, anxiety disorders and stroke.

A further object of the invention is a method for the treatment of schizophrenia, obsessive-compulsive personality disorder, major depression, bipolar disorders, anxiety disorders, normal aging, epilepsy, retinal degeneration, traumatic brain injury, spinal cord injury, post-traumatic stress disorder, panic disorder, Parkinson's disease, dementia, Alzheimer's disease, cognitive impairment, chemotherapy-induced cognitive dysfunction, Down syndrome, autism spectrum disorders, hearing loss, tinnitus, spinocerebellar ataxia, amyotrophic lateral sclerosis, multiple sclerosis, Huntington's disease, stroke, radiation therapy, chronic stress, abuse of neuro-active drugs, such as alcohol, opiates, methamphetamine, phencyclidine and cocaine, which method comprises administering an effective amount of a compound of formula I.

One embodiment of the invention is compounds of formula Ia

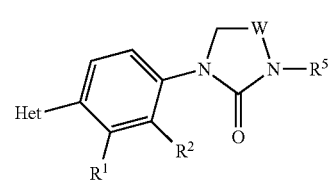

Ia wherein
Het is oxazole-5-yl, pyridin-4-yl, or pyrazol-4-yl;
$R^1$ and $R^2$ are each independently hydrogen, lower alkyl, lower alkoxy, or halogen;
W is —CH$_2$— or —CH$_2$CH$_2$—;
$R^5$ is CHR-phenyl or CH$_2$CHR-phenyl, optionally substituted by halogen, lower alkoxy, lower alkyl substituted by halogen, lower alkoxy substituted by halogen or lower alkyl, or is CHR-pyridin-2-yl, CHR-pyridin-3-yl or CHR-pyridin-4-yl;
R is hydrogen or lower alkyl;
or a pharmaceutically acceptable acid addition salt, a racemic mixture or its corresponding enantiomer and/or optical isomer thereof Another embodiment of the invention are further compounds of formula Ia-1,

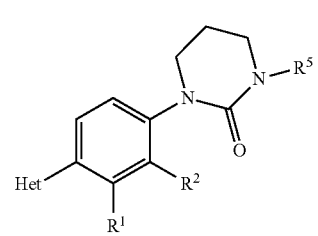

Ia-1 wherein
Het is oxazole-5-yl, pyridin-4-yl, or pyrazol-4-yl;
$R^1$ and $R^2$ are each independently hydrogen, lower alkyl, lower alkoxy, or halogen;
$R^5$ is CHR-phenyl or CH$_2$CHR-phenyl, optionally substituted by halogen, lower alkoxy, lower alkyl substituted by halogen, lower alkoxy substituted by halogen or lower alkyl, or is CHR-pyridin-2-yl, CHR-pyridin-3-yl or CHR-pyridin-4-yl;
R is hydrogen or lower alkyl;
or a pharmaceutically acceptable acid addition salt, a racemic mixture or its corresponding enantiomer and/or optical isomer thereof.

For example the following compounds of formula Ia-1 are embodiments of the invention:
1-benzyl-3-[3-methoxy-4-(1H-pyrazol-4-yl)phenyl]hexahydropyrimidin-2-one;
1-[(2-chlorophenyl)methyl]-3-[3-methoxy-4-(1H-pyrazol-4-yl)phenyl]hexahydropyrimidin-2-one; or,
1-[(3-methoxyphenyl)methyl]-3-[3-methoxy-4-(1H-pyrazol-4-yl)phenyl]hexahydropyrimidin-2-one.

Another embodiment the invention are further compounds of formula Ia-2,

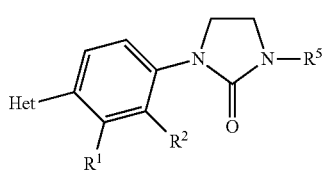

Ia-2 wherein
Het is oxazole-5-yl, pyridin-4-yl, or pyrazol-4-yl;
R¹ and R² are, independently from each other, hydrogen, lower alkyl, lower alkoxy, or halogen;
R⁵ is CHR-phenyl or CH₂CHR-phenyl, optionally substituted by halogen, lower alkoxy, lower alkyl substituted by halogen, lower alkoxy substituted by halogen or lower alkyl, or is CHR-pyridin-2-yl, CHR-pyridin-3-yl or CHR-pyridin-4-yl;
R is hydrogen or lower alkyl;
or a pharmaceutically acceptable acid addition salt, a racemic mixture or its corresponding enantiomer and/or optical isomer thereof.

For example the following compounds of formula Ia-2 are embodiments of the invention:

1-benzyl-3-(4-(pyridin-4-yl)phenyl)imidazolidin-2-one;
1-benzyl-3-[3-methoxy-4-(1H-pyrazol-4-yl)phenyl]imidazolidin-2-one;
1-[(2-chlorophenyl)methyl]-3-[3-methoxy-4-(1H-pyrazol-4-yl)phenyl]imidazolidin-2-one;
1-[(3-methoxyphenyl)methyl]-3-[3-methoxy-4-(1H-pyrazol-4-yl)phenyl]imidazolidin-2-one;
1-[(3-chlorophenyl)methyl]-3-[3-methoxy-4-(1H-pyrazol-4-yl)phenyl]imidazolidin-2-one;
1-[(3-fluorophenyl)methyl]-3-[3-methoxy-4-(1H-pyrazol-4-yl)phenyl]imidazolidin-2-one;
1-[3-methoxy-4-(1H-pyrazol-4-yl)phenyl]-3-[[3-(trifluoromethyl)phenyl]methyl]imidazolidin-2-one;
1-[3-methoxy-4-(1H-pyrazol-4-yl)phenyl]-3-[[3-(trifluoromethoxy)phenyl]methyl]imidazolidin-2-one;
1-[(3-ethoxyphenyl)methyl]-3-[3-methoxy-4-(1H-pyrazol-4-yl)phenyl]imidazolidin-2-one
1-[(3-methoxyphenyl)methyl]-3-[4-(1H-pyrazol-4-yl)phenyl]imidazolidin-2-one;
1-[(3-methoxyphenyl)methyl]-3-[3-methyl-4-(1H-pyrazol-4-yl)phenyl]imidazolidin-2-one;
1-[3-chloro-4-(1H-pyrazol-4-yl)phenyl]-3-[(3-methoxyphenyl)methyl]imidazolidin-2-one;
1-[2-fluoro-4-(1H-pyrazol-4-yl)phenyl]-3-[(3-methoxyphenyl)methyl]imidazolidin-2-one;
1-[3-fluoro-4-(1H-pyrazol-4-yl)phenyl]-3-[(3-methoxyphenyl)methyl]imidazolidin-2-one;
1-[3-ethoxy-4-(1H-pyrazol-4-yl)phenyl]-3-[(3-methoxyphenyl)methyl]imidazolidin-2-one;
1-[(2-fluorophenyl)methyl]-3-[3-methoxy-4-(1H-pyrazol-4-yl)phenyl]imidazolidin-2-one;
1-[3-methoxy-4-(1H-pyrazol-4-yl)phenyl]-3-(o-tolylmethyl)imidazolidin-2-one;
1-[3-methoxy-4-(1H-pyrazol-4-yl)phenyl]-3-(m-tolylmethyl)imidazolidin-2-one;
1-[(3-methoxyphenyl)methyl]-3-[2-methoxy-4-(1H-pyrazol-4-yl)phenyl]imidazolidin-2-one;
1-[(2-methoxyphenyl)methyl]-3-[3-methoxy-4-(1H-pyrazol-4-yl)phenyl]imidazolidin-2-one;
1-[3-methoxy-4-(1H-pyrazol-4-yl)phenyl]-3-(2-phenylethyl)imidazolidin-2-one;
1-[2-(2-methoxyphenyl)ethyl]-3-[3-methoxy-4-(1H-pyrazol-4-yl)phenyl]imidazolidin-2-one;
1-[2-(2-chlorophenyl)ethyl]-3-[3-methoxy-4-(1H-pyrazol-4-yl)phenyl]imidazolidin-2-one;
1-[2-chloro-4-(1H-pyrazol-4-yl)phenyl]-3-[(3-methoxyphenyl)methyl]imidazolidin-2-one;
1-[(4-fluorophenyl)methyl]-3-[3-methoxy-4-(1H-pyrazol-4-yl)phenyl]imidazolidin-2-one;
1-[3-methoxy-4-(1H-pyrazol-4-yl)phenyl]-3-(3-pyridylmethyl)imidazolidin-2-one;
1-[2-(3-chlorophenyl)ethyl]-3-[3-methoxy-4-(1H-pyrazol-4-yl)phenyl]imidazolidin-2-one;
1-[2-(4-chlorophenyl)ethyl]-3-[3-methoxy-4-(1H-pyrazol-4-yl)phenyl]imidazolidin-2-one;
1-[3-methoxy-4-(1H-pyrazol-4-yl)phenyl]-3-(1-phenylpropyl)imidazolidin-2-one;
1-[3-methoxy-4-(4-pyridyl)phenyl]-3-[[2-(trifluoromethyl)phenyl]methyl]imidazolidin-2-one;
1-[3-methoxy-4-(4-pyridyl)phenyl]-3-(4-pyridylmethyl)imidazolidin-2-one;
1-[(3-methoxyphenyl)methyl]-3-[4-(1,3-oxazol-5-yl)phenyl]imidazolidin-2-one;
1-[3-methoxy-4-(1H-pyrazol-4-yl)phenyl]-3-(4-pyridylmethyl)imidazolidin-2-one;
1-[3-methoxy-4-(1H-pyrazol-4-yl)phenyl]-3-(2-pyridylmethyl)imidazolidin-2-one;
1-[3-methoxy-4-(1H-pyrazol-4-yl)phenyl]-3-(2-phenylpropyl)imidazolidin-2-one;
1-[3-methoxy-4-(4-pyridyl)phenyl]-3-(m-tolylmethyl)imidazolidin-2-one;
1-[3-methoxy-4-(4-pyridyl)phenyl]-3-(3-pyridylmethyl)imidazolidin-2-one;
1-[3-methoxy-4-(1,3-oxazol-5-yl)phenyl]-3-[(2-methoxyphenyl)methyl]imidazolidin-2-one;
1-[3-methoxy-4-(1,3-oxazol-5-yl)phenyl]-3-[(3-methoxyphenyl)methyl]imidazolidin-2-one;
1-[(2-chlorophenyl)methyl]-3-[3-methoxy-4-(1,3-oxazol-5-yl)phenyl]imidazolidin-2-one;
1-[(3-fluorophenyl)methyl]-3-[4-(1,3-oxazol-5-yl)phenyl]imidazolidin-2-one;
1-[(2-fluorophenyl)methyl]-3-[4-(1,3-oxazol-5-yl)phenyl]imidazolidin-2-one;
1-[(2-fluorophenyl)methyl]-3-[3-methoxy-4-(1,3-oxazol-5-yl)phenyl]imidazolidin-2-one; or
1-[(3-fluorophenyl)methyl]-3-[3-methoxy-4-(1,3-oxazol-5-yl)phenyl]imidazolidin-2-one.

A further embodiment of the invention are compounds of formula Ib

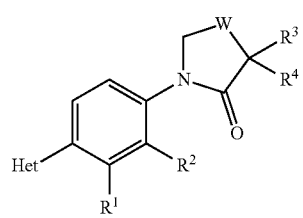

Ib wherein
Het is oxazole-5-yl, pyridin-4-yl, or pyrazol-4-yl;
R¹ and R² are each independently hydrogen, lower alkyl, lower alkoxy, or halogen;
W is —CH₂— or —CH₂CH₂—;
R³ is hydrogen or lower alkyl;

R⁴ is —(CH₂)ₙ-phenyl, optionally substituted by halogen, lower alkoxy, lower alkyl substituted by halogen, lower alkoxy substituted by halogen or lower alkyl;
n is 0 or 1;
or a pharmaceutically acceptable acid addition salt, a racemic mixture or its corresponding enantiomer and/or optical isomer thereof.

A further embodiment of the invention are compounds of formula Ib-1

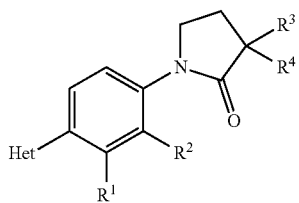

wherein
Het is oxazole-5-yl, pyridin-4-yl, or pyrazol-4-yl;
R¹ and R² are each independently hydrogen, lower alkyl, lower alkoxy, or halogen;
R³ is hydrogen or lower alkyl;
R⁴ is —(CH₂)ₙ-phenyl, optionally substituted by halogen, lower alkoxy, lower alkyl substituted by halogen, lower alkoxy substituted by halogen or lower alkyl;
n is 0 or 1;
or a pharmaceutically acceptable acid addition salt, a racemic mixture or its corresponding enantiomer and/or optical isomer thereof.

For example the following compounds of formula Ib-1 are embodiments of the invention:
3-ethyl-1-(3-methoxy-4-(oxazol-5-yl)phenyl)-3-phenylpyrrolidin-2-one
1-(3-methoxy-4-oxazol-5-yl-phenyl)-3-(3-methoxyphenyl)pyrrolidin-2-one
3-(2-chlorophenyl)-1-(3-methoxy-4-oxazol-5-yl-phenyl)pyrrolidin-2-one
1-(3-methoxy-4-oxazol-5-yl-phenyl)-3-phenyl-pyrrolidin-2-one
1-[3-methoxy-4-(1H-pyrazol-4-yl)phenyl]-3-phenyl-pyrrolidin-2-one
3-phenyl-1-[4-(1H-pyrazol-4-yl)phenyl]pyrrolidin-2-one
3-(3-methoxyphenyl)-1-[4-(1H-pyrazol-4-yl)phenyl]pyrrolidin-2-one
3-(4-chlorophenyl)-1-[4-(1H-pyrazol-4-yl)phenyl]pyrrolidin-2-one
3-(4-fluorophenyl)-1-[4-(1H-pyrazol-4-yl)phenyl]pyrrolidin-2-one
3-(3-chlorophenyl)-1-[4-(1H-pyrazol-4-yl)phenyl]pyrrolidin-2-one
3-benzyl-1-(3-methoxy-4-(1H-pyrazol-4-yl)phenyl)pyrrolidin-2-one
1-(3-methoxy-4-(1H-pyrazol-4-yl)phenyl)-3-(3-methoxyphenyl)pyrrolidin-2-one
3-(3-chlorophenyl)-1-(3-methoxy-4-(1H-pyrazol-4-yl)phenyl)pyrrolidin-2-one
3-(3-fluorophenyl)-1-(3-methoxy-4-(1H-pyrazol-4-yl)phenyl)pyrrolidin-2-one
3-[(3-chlorophenyl)methyl]-1-[3-methoxy-4-(1H-pyrazol-4-yl)phenyl]pyrrolidin-2-one
3-[(2-chlorophenyl)methyl]-1-[3-methoxy-4-(1H-pyrazol-4-yl)phenyl]pyrrolidin-2-one
3-(3-chlorophenyl)-1-[3-methoxy-4-(1,3-oxazol-5-yl)phenyl]pyrrolidin-2-one
3-[(3-methoxyphenyl)methyl]-1-[3-methoxy-4-(1H-pyrazol-4-yl)phenyl]pyrrolidin-2-one
1-[3-methoxy-4-(1,3-oxazol-5-yl)phenyl]-3-(2-methoxyphenyl)pyrrolidin-2-one
3-(3-methoxyphenyl)-1-[4-(1,3-oxazol-5-yl)phenyl]pyrrolidin-2-one
1-[4-(1,3-oxazol-5-yl)phenyl]-3-phenylpyrrolidin-2-one
1-[3-methoxy-4-(1,3-oxazol-5-yl)phenyl]-3-[3-(trifluoromethyl)phenyl]pyrrolidin-2-one
3-(2-fluorophenyl)-1-[4-(1,3-oxazol-5-yl)phenyl]pyrrolidin-2-one
3-(2-fluorophenyl)-1-[3-methoxy-4-(1,3-oxazol-5-yl)phenyl]pyrrolidin-2-one
3-(3-fluorophenyl)-1-[4-(1,3-oxazol-5-yl)phenyl]pyrrolidin-2-one
3-(3-fluorophenyl)-1-[3-methoxy-4-(1,3-oxazol-5-yl)phenyl]pyrrolidin-2-one
3-(3-methoxyphenyl)-1-(3-methoxy-4-pyridin-4-ylphenyl)pyrrolidin-2-one or
3-(3-methoxyphenyl)-1-(4-pyridin-4-ylphenyl)pyrrolidin-2-one.

One further embodiment of the present invention are compounds of formula Ib-2

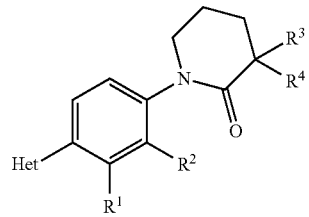

wherein
Het is oxazole-5-yl, pyridin-4-yl, or pyrazol-4-yl;
R¹ and R² are each independently hydrogen, lower alkyl, lower alkoxy, or halogen;
R³ is hydrogen or lower alkyl;
R⁴ is —(CH₂)ₙ-phenyl, optionally substituted by halogen, lower alkoxy, lower alkyl substituted by halogen, lower alkoxy substituted by halogen or lower alkyl;
n is 0 or 1;
or a pharmaceutically acceptable acid addition salt, a racemic mixture or its corresponding enantiomer and/or optical isomer thereof.

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, and isopropyl.

The term "alkoxy" denotes a group —O—R' wherein R' is lower alkyl as defined above.

The term "lower alkyl substituted by halogen" denotes a lower alkyl group as defined above, wherein at least one hydrogen atom is replaced by a halogen atom. The preferred group is CF₃.

The term "lower alkoxy substituted by halogen" denotes a lower alkoxy group as defined above, wherein at least one hydrogen atom is replaced by a halogen atom. The preferred group is OCF₃.

The term "halogen" denotes chlorine, bromine, fluorine or iodine.

The term "leaving group" (LG) has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, mesyloxy, tosyloxy, trifluoromethanesulfonyloxy and the like.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

Compounds of formula I can be prepared according to the below process steps and in accordance with Schemes 1-7.

The present new compounds of formula I and their pharmaceutically acceptable salts can be prepared by methods known in the art, for example, by processes described below, which process comprises a) reacting a compound of formula

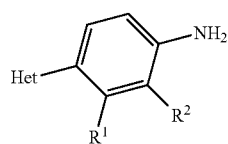

with a compound of formula

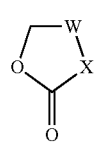

to a compound of formula

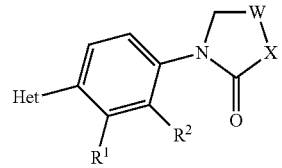

I and, if desired, converting the compounds obtained into pharmaceutically acceptable acid addition salts, or b) reacting a compound of formula

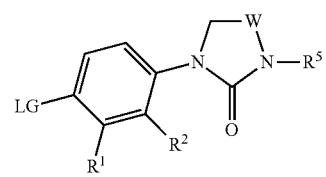

5 with a compound of formula

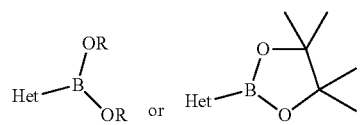

6 wherein R is hydrogen or lower alkyl, to afford a compound of formula Ia

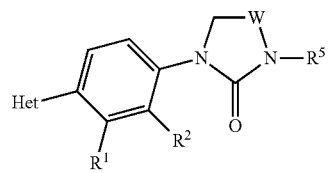

Ia and, if desired, converting the compounds obtained into pharmaceutically acceptable acid addition salts, or c) reacting a compound of formula

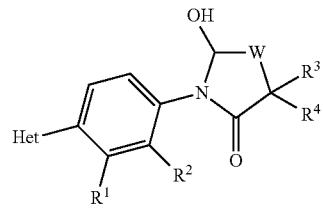

14 with a reducing agent, such as $Et_3SiH$ to afford a compound of formula Ib

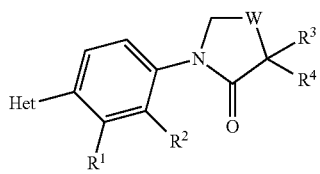

and, if desired, converting the compounds obtained into pharmaceutically acceptable acid addition salts.

The definitions of substituents is as described above.

The preparation of compounds of formula I of the present invention may be carried out in sequential or convergent synthetic routes. Syntheses of the compounds of the invention are shown in the following scheme 1. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

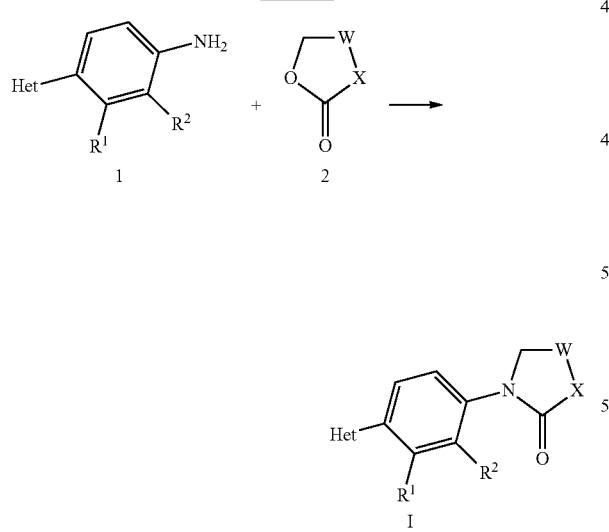

Compounds of formula I can be prepared according to Scheme 1, by reaction of an aromatic amine 1 with a lactone 2. Amine 1 may be treated with a suitable base, such as trimethylaluminum, for increased reactivity. Suitable starting materials 1 and 2 are commercially available or can be prepared by methods known in the art.

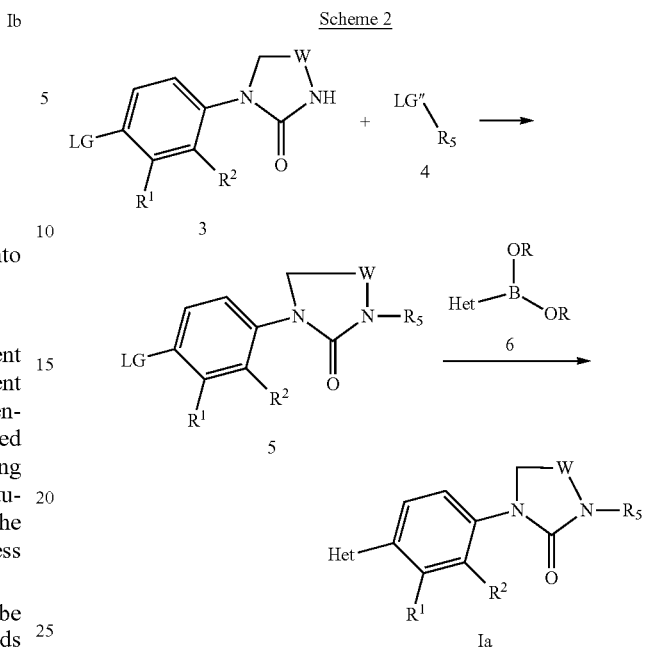

R is hydrogen or lower alkyl

Compounds of formula Ia can be prepared according to Scheme 2. An arylimidazole 3, in which LG is a suitable leaving group, such as Br, is first reacted with a suitable base, such as sodium hydride, and then with compound 4, in which LG" is a suitable leaving group, such as Br. The resulting compound 5 is then reacted with a boronic acid, or a boronic acid ester, 6, in the presence of a suitable catalyst, such as tetrakis(triphenylphosphine)palladium, and a suitable base, such as sodium carbonate, to give compound Ia. Arylimidazoles 3 are commercially available, can be prepared by methods known in the art, or can be prepared according to scheme 3.

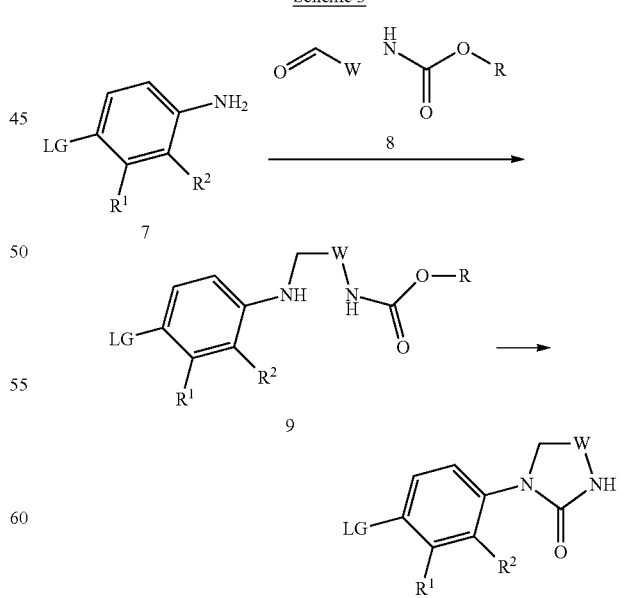

R = hydrogen or lower alkyl

Compounds of formula 3 can be prepared according to Scheme 3: An arylamine 7, in which LG is a suitable leaving group such as Br, is reacted with an alkoxycarbonylamino-aldehyde 8 and a reducing agent, such as NaBH(OAc)₃/ AcOH to give 9 in a process known as reductive amination. Compound 9 can be transformed into 3 by treatment with a suitable base such as KOtBu.

base, such as LiHMDS, and subsequently with allyl iodide to give 11. Acid 11 is treated with an activating agent, such as PyBOP, and converted with an aromatic amine 1 into 12. Compound 12 is then oxidized by suitable oxidizing agents, such as NMO, OsO₄, and NaIO₄ to give 14, possibly via a diol intermediate 13. Compound 14 is then reduced to compound Ib with a suitable reducing agent, such as Et₃SiH.

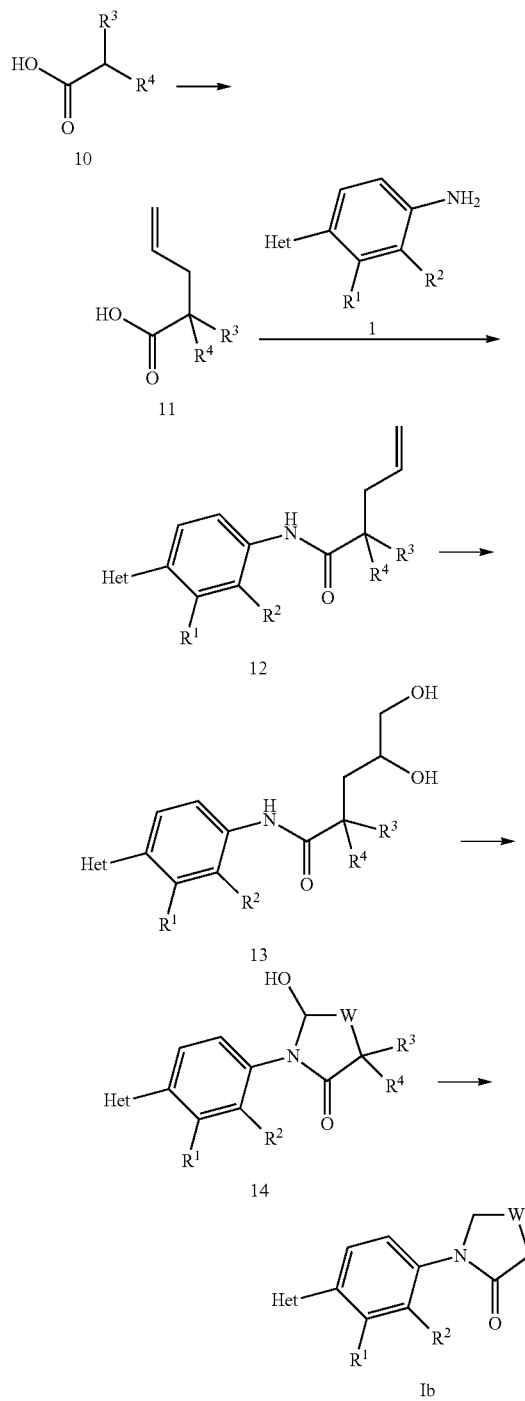

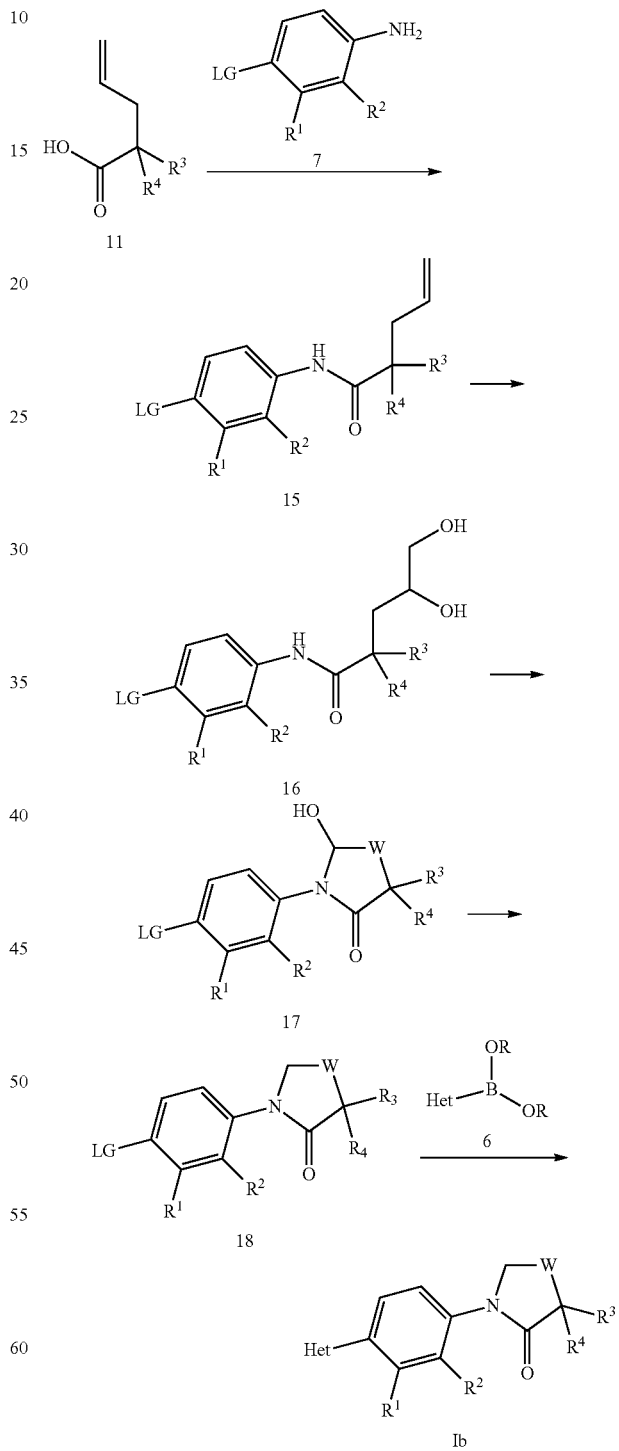

R is hydrogen or lower alkyl

Compounds of formula Ib can be prepared according to scheme 4. An arylacetic acid 10 is treated with a suitable Alternatively, compounds of formula Ib can be prepared according to scheme 5. Allylarylacetic acid 11 is treated with an activating agent, such as PyBOP, and converted with an aromatic amine 7, in which LG is a suitable leaving group, such as Br, into 15. In analogy to scheme 4, compound 15 is then oxidized by suitable oxidizing agents, such as NMO, $OsO_4$, and $NaIO_4$ to give 17, possibly via a diol intermediate 16. Compound 17 is then reduced to compound 18 with a suitable reducing agent, such as $Et_3SiH$. Compound 18 is then reacted with a boronic acid, or a boronic acid ester, 6, in the presence of a suitable catalyst, such as tetrakis(triphenylphosphine)palladium, and a suitable base, such as sodium carbonate, to give compound Ib.

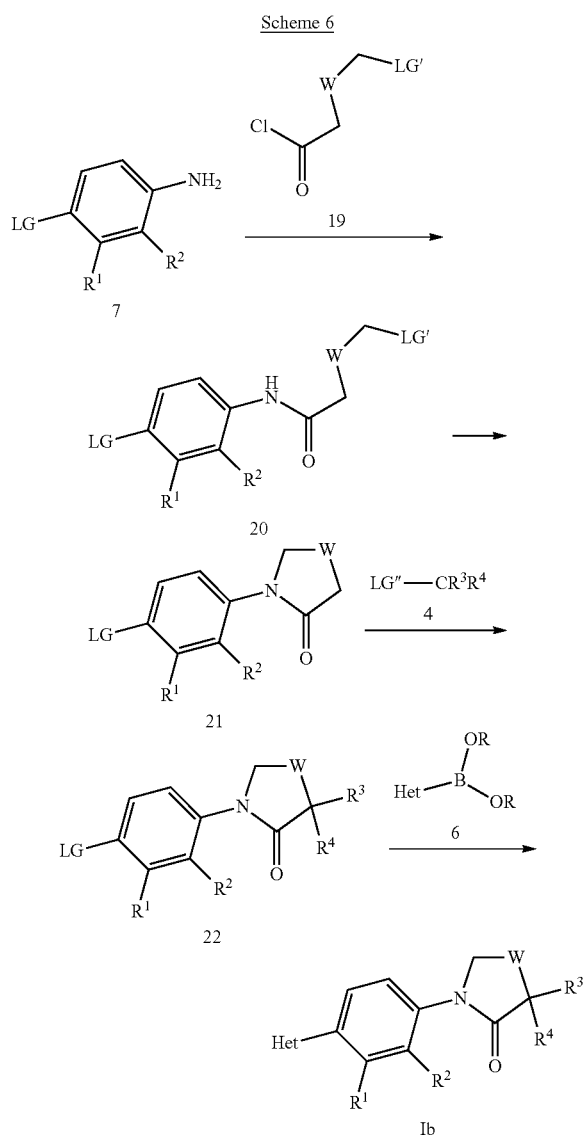

R is hydrogen or lower alkyl

Compounds of formula Ib can be prepared according to scheme 6. An arylamine 7, in which LG is a suitable leaving group such as Br, is reacted with an acid chloride 19, or a similarly activated acid, in which LG' is a suitable leaving group such as Br, to give 20. Treatment with a suitable base, such as KOH, furnishes 21. Treatment with another suitable base, such as a lithium amide, and compound 4, in which LG" is a suitable leaving group such as bromine, gives 22. Compound 22 is then reacted with a boronic acid, or a boronic acid ester, 6, in the presence of a suitable catalyst, such as tetrakis(triphenylphosphine)palladium, and a suitable base, such as sodium carbonate, to give compound Ib.

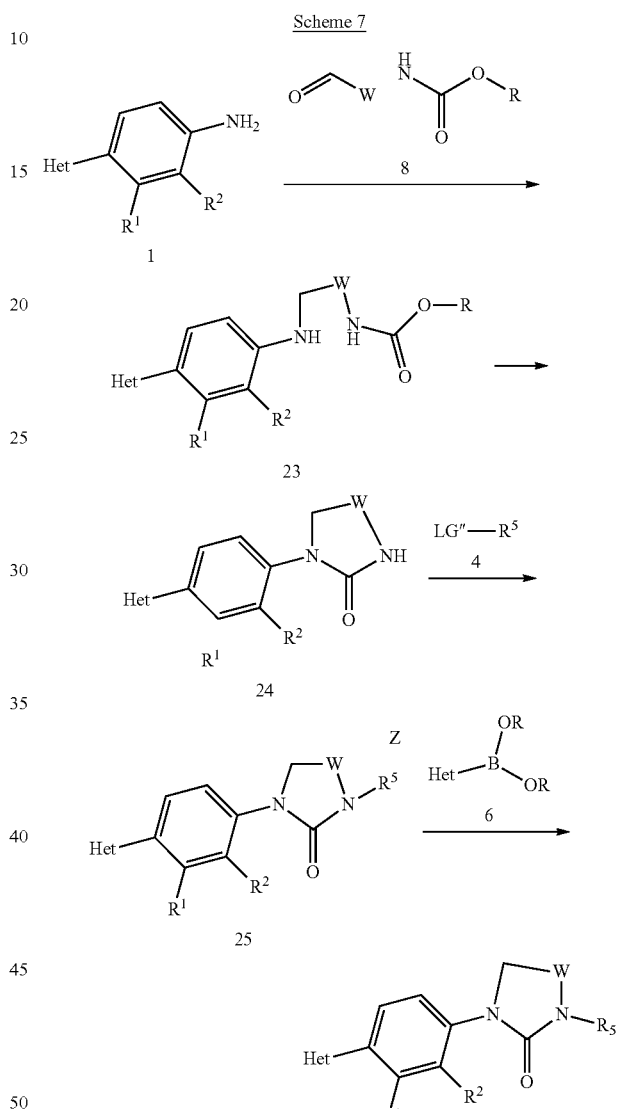

Compounds of formula Ia can also be prepared according to Scheme 7. An arylamine 1 is reacted with an alkoxycarbonylaminoaldehyde 8 and a reducing agent, such as $NaBH(OAc)_3$/AcOH to give 23 in a process known as reductive amination. Compound 23 can be transformed into 24 by treatment with a suitable base such as KOtBu. 23 is first reacted with a suitable base, such as sodium hydride, and then with compound 4, in which LG is a suitable leaving group, such as Br. The resulting compound 25 is then reacted with a boronic acid, or a boronic acid ester, 6, in the presence of a suitable catalyst, such as tetrakis(triphenylphosphine) palladium, and a suitable base, such as sodium carbonate, to give compound I-a.

Structure 6 in the schemes

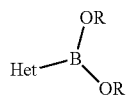

includes also the following structure:

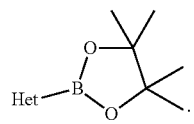

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention have an activity as neurogenic agents.

The compounds were investigated in accordance with the test given hereinafter.

Neurogenesis Assay

Neural Stem Cell Proliferation Assay

Neurogenic properties of small molecules are determined based on the proliferation of human embryonic stem cell derived neural stem cells (NSCs) which were derived via a dual smad inhibition as previously described (Chambers, S. M., et al., *Highly efficient neural conversion of human ES and iPS cells by dual inhibition of SMAD signaling*, Nature biotechnology, 2009 27(3): p. 275-80.).

Compounds response is measured by the increase in cells based on ATP levels (Promega:CellTiterGlo®) after an incubation period of 4 days. NSCs are thawed and expanded over 3 passages. On the $14^{th}$ day, NSCs are seeded in Polyornithin/Laminin coated 384 well plates at a cell density of 21,000 cells/$cm^2$ in a media volume of 38 μl.

4 hours after cell seeding, compound solutions are added at a volume of 2 μl. Stock solutions of the compounds (water, 5% DMSO) are diluted to obtain a dose response (11 points, dilution factor is 2), ranging from 8 μM to 8 nM. Controls are run to consistently determine the neurogenic properties of the cells:

Negative (neutral) control is cell culture Media (final DMSO concentration: 0.25%).

Positive controls are:
1. cell culture Media+100 ng/ml FGF2 (final DMSO concentration: 0.1%)
2. cell culture Media+20 ng/ml EGF (final DMSO concentration: 0.1%)
3. cell culture Media+100 ng/ml Wnt3a (final DMSO concentration: 0.1%)

After 4 days incubation at 37° C., 5% $CO_2$, the amount of ATP per well is quantified. The ATP concentration is proportional to the cell number. ATP is quantified by using the Promega CellTiterGlo® kit. The CellTiterGlo® reagents contain a cell lysis buffer, a thermo stable luciferase (Ultra-Glo™ recombinant luciferase), magnesium and luciferin. Luciferin reacts with ATP producing oxyluciferin, AMP and light. The luminescence signal is proportional to the ATP content.

The value of negative (neutral) control is determined for each assay plate by taking the average of 16 negative control wells. The neurogenic compound response is calculated for each compound as (compound/Negative Control)*100. The values of $EC_{150}$ from the dose response curve are determined for each test compound. The EC150 is the compound concentration at which 150% activity of control (100%) is reached. The preferred compounds show a $EC_{150}$ (μM) in the range of <3.0 μM as shown in Table 1.

TABLE 1

List of examples and $EC_{150}$ data

| Expl. No | Compound name | $EC_{150}$(uM) |
|---|---|---|
| 1 | 3-Ethyl-1-(3-methoxy-4-(oxazol-5-yl)phenyl)-3-phenylpyrrolidin-2-one | 3.2257 |
| 2 | 1-Benzyl-3-(4-(pyridin-4-yl)phenyl)imidazolidin-2-one | 1.0425 |
| 3 | 1-(3-Methoxy-4-oxazol-5-yl-phenyl)-3-(3-methoxyphenyl)pyrrolidin-2-one | 0.0814 |

TABLE 1-continued

List of examples and EC$_{150}$ data

| Expl. No | Compound name | EC$_{150}$(uM) |
|---|---|---|
| 4 | 3-(2-Chlorophenyl)-1-(3-methoxy-4-oxazol-5-yl-phenyl)pyrrolidin-2-one | 0.6783 |
| 5 | 1-Benzyl-3-[3-methoxy-4-(1H-pyrazol-4-yl)phenyl]hexahydropyrimidin-2-one | 1.3254 |
| 6 | 1-[(2-Chlorophenyl)methyl]-3-[3-methoxy-4-(1H-pyrazol-4-yl)phenyl]hexahydropyrimidin-2-one | 1.9918 |
| 7 | 1-[(3-Methoxyphenyl)methyl]-3-[3-methoxy-4-(1H-pyrazol-4-yl)phenyl]hexahydropyrimidin-2-one | 0.1144 |
| 8 | 1-(3-Methoxy-4-oxazol-5-yl-phenyl)-3-phenyl-pyrrolidin-2-one | 0.4712 |
| 9 | 1-Benzyl-3-[3-methoxy-4-(1H-pyrazol-4-yl)phenyl]imidazolidin-2-one | 0.1612 |
| 10 | 1-[(2-Chlorophenyl)methyl]-3-[3-methoxy-4-(1H-pyrazol-4-yl)phenyl]imidazolidin-2-one | 0.2695 |
| 11 | 1-[(3-Methoxyphenyl)methyl]-3-[3-methoxy-4-(1H-pyrazol-4-yl)phenyl]imidazolidin-2-one | 0.0239 |
| 12 | 1-[3-Methoxy-4-(1H-pyrazol-4-yl)phenyl]-3-phenyl-pyrrolidin-2-one | 0.0414 |
| 13 | 3-Phenyl-1-[4-(1H-pyrazol-4-yl)phenyl]pyrrolidin-2-one | 0.2048 |
| 14 | 3-(3-Methoxyphenyl)-1-[4-(1H-pyrazol-4-yl)phenyl]pyrrolidin-2-one | 0.0405 |
| 15 | 3-(4-Chlorophenyl)-1-[4-(1H-pyrazol-4-yl)phenyl]pyrrolidin-2-one | 0.384 |
| 16 | 3-(4-Fluorophenyl)-1-[4-(1H-pyrazol-4-yl)phenyl]pyrrolidin-2-one | 0.0417 |
| 17 | 3-(3-Chlorophenyl)-1-[4-(1H-pyrazol-4-yl)phenyl]pyrrolidin-2-one | 0.2304 |
| 18 | 1-[(3-chlorophenyl)methyl]-3-[3-methoxy-4-(1H-pyrazol-4-yl)phenyl]imidazolidin-2-one | 0.3946 |
| 19 | 1-[(3-Fluorophenyl)methyl]-3-[3-methoxy-4-(1H-pyrazol-4-yl)phenyl]imidazolidin-2-one | 0.047 |
| 20 | 1-[3-Methoxy-4-(1H-pyrazol-4-yl)phenyl]-3-[[3-(trifluoromethyl)phenyl]methyl]imidazolidin-2-one | 0.0086 |
| 21 | 1-[3-Methoxy-4-(1H-pyrazol-4-yl)phenyl]-3-[[3-(trifluoromethoxy)phenyl]methyl]imidazolidin-2-one | 0.0092 |
| 22 | 1-[(3-Ethoxyphenyl)methyl]-3-[3-methoxy-4-(1H-pyrazol-4-yl)phenyl]imidazolidin-2-one | 0.0739 |
| 23 | 3-Benzyl-1-(3-methoxy-4-(1H-pyrazol-4-yl)phenyl)pyrrolidin-2-one | 0.6122 |
| 24 | 1-(3-Methoxy-4-(1H-pyrazol-4-yl)phenyl)-3-(3-methoxyphenyl)pyrrolidin-2-one | 0.0299 |
| 25 | 3-(3-Chlorophenyl)-1-(3-methoxy-4-(1H-pyrazol-4-yl)phenyl)pyrrolidin-2-one | 0.0659 |
| 26 | 3-(3-Fluorophenyl)-1-(3-methoxy-4-(1H-pyrazol-4-yl)phenyl)pyrrolidin-2-one | 0.0776 |
| 27 | 1-[(3-Methoxyphenyl)methyl]-3-[4-(1H-pyrazol-4-yl)phenyl]imidazolidin-2-one | 0.2944 |
| 28 | 1-[(3-Methoxyphenyl)methyl]-3-[3-methyl-4-(1H-pyrazol-4-yl)phenyl]imidazolidin-2-one | 1.2174 |
| 29 | 1-[3-Chloro-4-(1H-pyrazol-4-yl)phenyl]-3-[(3-methoxyphenyl)methyl]imidazolidin-2-one | 0.3664 |
| 30 | 1-[2-Fluoro-4-(1H-pyrazol-4-yl)phenyl]-3-[(3-methoxyphenyl)methyl]imidazolidin-2-one | 0.0416 |
| 31 | 1-[3-Fluoro-4-(1H-pyrazol-4-yl)phenyl]-3-[(3-methoxyphenyl)methyl]imidazolidin-2-one | 0.0157 |
| 32 | 1-[3-Ethoxy-4-(1H-pyrazol-4-yl)phenyl]-3-[(3-methoxyphenyl)methyl]imidazolidin-2-one | 0.8349 |
| 33 | 1-[(2-Fluorophenyl)methyl]-3-[3-methoxy-4-(1H-pyrazol-4-yl)phenyl]imidazolidin-2-one | 0.2246 |
| 34 | 1-[3-Methoxy-4-(1H-pyrazol-4-yl)phenyl]-3-(o-tolylmethyl)imidazolidin-2-one | 0.2004 |
| 35 | 1-[3-Methoxy-4-(1H-pyrazol-4-yl)phenyl]-3-(m-tolylmethyl)imidazolidin-2-one | 2.6464 |
| 36 | 3-[(3-Chlorophenyl)methyl]-1-[3-methoxy-4-(1H-pyrazol-4-yl)phenyl]pyrrolidin-2-one | 1.6485 |
| 37 | 3-[(2-Chlorophenyl)methyl]-1-[3-methoxy-4-(1H-pyrazol-4-yl)phenyl]pyrrolidin-2-one | 1.1254 |
| 38 | 3-(3-Chlorophenyl)-1-[3-methoxy-4-(1,3-oxazol-5-yl)phenyl]pyrrolidin-2-one | 1.3515 |
| 39 | 1-[(3-Methoxyphenyl)methyl]-3-[2-methoxy-4-(1H-pyrazol-4-yl)phenyl]imidazolidin-2-one | 0.393 |
| 40 | 3-[(3-Methoxyphenyl)methyl]-1-[3-methoxy-4-(1H-pyrazol-4-yl)phenyl]pyrrolidin-2-one | 0.334 |
| 41 | 1-[3-Methoxy-4-(1,3-oxazol-5-yl)phenyl]-3-(2-methoxyphenyl)pyrrolidin-2-one | 2.9106 |
| 42 | 1-[(2-Methoxyphenyl)methyl]-3-[3-methoxy-4-(1H-pyrazol-4-yl)phenyl]imidazolidin-2-one | 0.3085 |
| 43 | 1-[3-Methoxy-4-(1H-pyrazol-4-yl)phenyl]-3-(2-phenylethyl)imidazolidin-2-one | 0.3093 |
| 44 | 1-[2-(2-Methoxyphenyl)ethyl]-3-[3-methoxy-4-(1H-pyrazol-4-yl)phenyl]imidazolidin-2-one | 1.9784 |
| 45 | 1-[2-(2-Chlorophenyl)ethyl]-3-[3-methoxy-4-(1H-pyrazol-4-yl)phenyl]imidazolidin-2-one | 0.1358 |

TABLE 1-continued

List of examples and $EC_{150}$ data

| Expl. No | Compound name | $EC_{150}$(uM) |
|---|---|---|
| 46 | 1-[2-Chloro-4-(1H-pyrazol-4-yl)phenyl]-3-[(3-methoxyphenyl)methyl]imidazolidin-2-one | 1.8344 |
| 47 | 1-[(4-Fluorophenyl)methyl]-3-[3-methoxy-4-(1H-pyrazol-4-yl)phenyl]imidazolidin-2-one | 0.7685 |
| 48 | 1-[3-Methoxy-4-(1H-pyrazol-4-yl)phenyl]-3-(3-pyridylmethyl)imidazolidin-2-one | 0.1195 |
| 49 | 1-[2-(3-Chlorophenyl)ethyl]-3-[3-methoxy-4-(1H-pyrazol-4-yl)phenyl]imidazolidin-2-one | 1.7318 |
| 50 | 1-[2-(4-Chlorophenyl)ethyl]-3-[3-methoxy-4-(1H-pyrazol-4-yl)phenyl]imidazolidin-2-one | 2.0118 |
| 51 | 1-[3-Methoxy-4-(1H-pyrazol-4-yl)phenyl]-3-(1-phenylpropyl)imidazolidin-2-one | 0.5942 |
| 52 | 3-(3-Methoxyphenyl)-1-[4-(1,3-oxazol-5-yl)phenyl]pyrrolidin-2-one | 0.5169 |
| 53 | 1-[4-(1,3-Oxazol-5-yl)phenyl]-3-phenylpyrrolidin-2-one | 2.2077 |
| 54 | 1-[3-Methoxy-4-(4-pyridyl)phenyl]-3-[[2-(trifluoromethyl)phenyl]methyl]imidazolidin-2-one | 0.0351 |
| 55 | 1-[3-Methoxy-4-(4-pyridyl)phenyl]-3-(4-pyridylmethyl)imidazolidin-2-one | 0.3765 |
| 56 | 1-[3-Methoxy-4-(1,3-oxazol-5-yl)phenyl]-3-[3-(trifluoromethyl)phenyl]pyrrolidin-2-one | 1.8592 |
| 57 | 3-(2-Fluorophenyl)-1-[4-(1,3-oxazol-5-yl)phenyl]pyrrolidin-2-one | 0.525 |
| 58 | 3-(2-Fluorophenyl)-1-[3-methoxy-4-(1,3-oxazol-5-yl)phenyl]pyrrolidin-2-one | 0.2297 |
| 59 | 1-[(3-Methoxyphenyl)methyl]-3-[4-(1,3-oxazol-5-yl)phenyl]imidazolidin-2-one | 0.1225 |
| 60 | 3-(3-Fluorophenyl)-1-[4-(1,3-oxazol-5-yl)phenyl]pyrrolidin-2-one | 0.6045 |
| 61 | 3-(3-Fluorophenyl)-1-[3-methoxy-4-(1,3-oxazol-5-yl)phenyl]pyrrolidin-2-one | 0.2623 |
| 62 | 1-[3-Methoxy-4-(1H-pyrazol-4-yl)phenyl]-3-(4-pyridylmethyl)imidazolidin-2-one | 0.042 |
| 63 | 1-[3-Methoxy-4-(1H-pyrazol-4-yl)phenyl]-3-(2-pyridylmethyl)imidazolidin-2-one | 0.2551 |
| 64 | 1-[3-Methoxy-4-(1H-pyrazol-4-yl)phenyl]-3-(2-phenylpropyl)imidazolidin-2-one | 0.3873 |
| 65 | 1-[3-Methoxy-4-(4-pyridyl)phenyl]-3-(m-tolylmethyl)imidazolidin-2-one | 0.0298 |
| 66 | 1-[3-Methoxy-4-(4-pyridyl)phenyl]-3-(3-pyridylmethyl)imidazolidin-2-one | 0.4002 |
| 67 | 1-[3-Methoxy-4-(1,3-oxazol-5-yl)phenyl]-3-[(2-methoxyphenyl)methyl]imidazolidin-2-one | 0.7015 |
| 68 | 1-[3-Methoxy-4-(1,3-oxazol-5-yl)phenyl]-3-[(3-methoxyphenyl)methyl]imidazolidin-2-one | 0.3158 |
| 69 | 1-[(2-Chlorophenyl)methyl]-3-[3-methoxy-4-(1,3-oxazol-5-yl)phenyl]imidazolidin-2-one | 2.2373 |
| 70 | 3-(3-Methoxyphenyl)-1-(3-methoxy-4-pyridin-4-ylphenyl)pyrrolidin-2-one | 0.0613 |
| 71 | 3-(3-Methoxyphenyl)-1-(4-pyridin-4-ylphenyl)pyrrolidin-2-one | 0.0155 |
| 72 | 1-[(3-Fluorophenyl)methyl]-3-[4-(1,3-oxazol-5-yl)phenyl]imidazolidin-2-one | 1.0717 |
| 73 | 1-[(2-Fluorophenyl)methyl]-3-[4-(1,3-oxazol-5-yl)phenyl]imidazolidin-2-one | 1.492 |
| 74 | 1-[(2-Fluorophenyl)methyl]-3-[3-methoxy-4-(1,3-oxazol-5-yl)phenyl]imidazolidin-2-one | 2.6998 |
| 75 | 1-[(3-Fluorophenyl)methyl]-3-[3-methoxy-4-(1,3-oxazol-5-yl)phenyl]imidazolidin-2-one | 0.5973 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules.

Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

Example 1

3-Ethyl-1-(3-methoxy-4-(oxazol-5-yl)phenyl)-3-phenylpyrrolidin-2-one

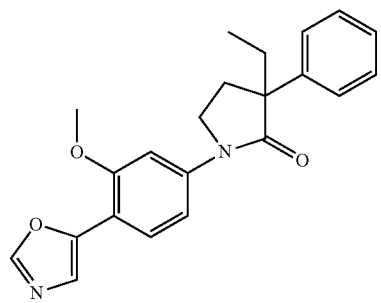 [SMILES: CCC1(c2ccccc2)CCN(c2ccc(-c3cnco3)c(OC)c2)C1=O]

In a 10 ml round-bottomed flask, 3-methoxy-4-(oxazol-5-yl)aniline (commercially available, CAS: 198821-79-3; 200 mg, 1.05 mmol) was combined with dioxane (4 ml) to give a light brown solution. Trimethylaluminum (2M in heptane, 1.05 ml, 2.1 mmol) was added. The reaction mixture was heated to 50° C. and stirred for 30 min. 3-Ethyl-3-phenyldihydrofuran-2(3H)-one (commercially available, CAS: 4064-16-8; 400 mg, 2.1 mmol) was added. The reaction mixture was heated to 100° C. and stirred for 2 d. The reaction mixture was poured into water/$Na_2CO_3$ and extracted with EtOAc (2×25 ml). The organic layers were dried over $Na_2SO_4$ and concentrated in vacuo. The crude material was purified by flash chromatography (silica gel, 20 g, 0% to 50% EtOAc in heptane) to yield the title compound as a light yellow waxy solid (221 mg, 58.0%). MS (m/e)=363.17 $[M+H]^+$.

Example 2

1-Benzyl-3-(4-(pyridin-4-yl)phenyl)imidazolidin-2-one

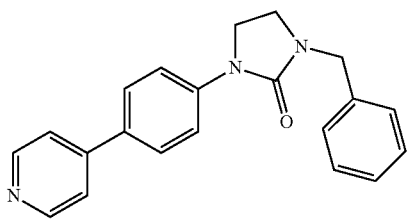 [SMILES: O=C1N(Cc2ccccc2)CCN1c1ccc(-c2ccncc2)cc1]

Step 1:
1-Benzyl-3-(4-bromophenyl)imidazolidin-2-one

In a 25 ml round-bottomed flask, 1-(4-bromophenyl)imidazolidin-2-one (commercially available, CAS: 530081-14-2; 480 mg, 1.99 mmol) was combined with DMF (10 ml) to give a light yellow solution. The reaction mixture was cooled to 0° C. Sodium hydride (159 mg, 3.98 mmol) was added. The reaction mixture was stirred 20 min at 0° C. The reaction mixture was allowed to warm to rt. (Bromomethyl)benzene (521 mg, 362 2.99 mmol) was added. The reaction mixture was stirred over night at rt. The reaction mixture was poured into water (40 ml) and extracted with EtOAc (3×40 ml). The organic layers were combined, washed with satd. NaCl (1×40 ml), dried over Na$_2$SO$_4$ and concentrated in vacuo. The crude material was purified by flash chromatography (silica gel, 20 g, 0% to 50% EtOAc in heptane) to yield the title compound as a white solid (629 mg, 95.4%). MS (m/e)=333.4 [M+H]$^+$.

Step 2: 1-Benzyl-3-(4-(pyridin-4-yl)phenyl)imidazolidin-2-one

In a 50 ml round-bottomed flask, a mixture of DMF/water (7:2) (22.5 ml) was deoxygenated with argon. 1-Benzyl-3-(4-bromophenyl)imidazolidin-2-one (200 mg, 604 µmol), pyridin-4-ylboronic acid (148 mg, 1.21 mmol), sodium carbonate (224 mg, 2.11 mmol) and tetrakis(triphenylphosphine)palladium (907 µg, 0.785 µmol) were added. The reaction mixture was heated to reflux and stirred over night. The reaction mixture was poured into water (50 ml) and extracted with EtOAc (3×50 ml). The organic layers were dried over Na$_2$SO$_4$ and concentrated in vacuo. The yellow solid residue was combined with MeOH (2 ml) and treated 5 min in the ultrasonic bath. The suspension was filtered. The white solid was dried in vacuo to yield the title compound as an off-white solid (89 mg, 44.6%). MS (m/e) =330.16 [M+H]$^+$.

Example 3

1-(3-Methoxy-4-oxazol-5-yl-phenyl)-3-(3-methoxyphenyl)pyrrolidin-2-one

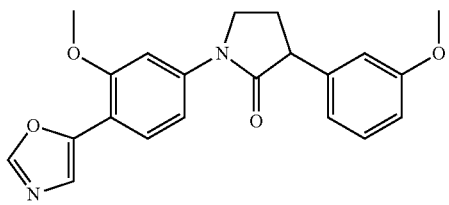 [SMILES: COc1cccc(C2CCN(c3ccc(-c4cnco4)c(OC)c3)C2=O)c1]

Step 1: 2-(3-Methoxyphenyl)pent-4-enoic acid

To a solution of 3-methoxyphenyl acetic acid (30.08 mmol) in THF (150 ml) at −78° C. was added LiHMDS (1M solution in THF; 66.19 ml, 66.19 mmol), and the reaction mixture was stirred at −78° C. for 0.5 h. Allyl iodide (2.75 ml, 30.08 mmol) was added to the reaction mixture at −78° C., and the mixture was slowly allowed to warm to 25° C. over a period of 3 h, and then continued to stir at 25° C. for 12 h. The reaction mixture was quenched with saturated ammonium chloride solution, acidified using 1N aqueous HCl solution, and extracted with EtOAc (2×130 ml). The combined organic layers were dried over anhydrous Na$_2$SO$_4$, filtered, and concentrated under reduced pressure. The resulting crude material was purified by column chromatography over silica gel (10-20% EtOAc/hexane) to get 2-(3-methoxyphenyl) pent-4-enoic acid (5.3 g, 85.48%) as light yellow oil.

Step 2: N-(3-Methoxy-4-oxazol-5-yl-phenyl)-2-(3-methoxyphenyl)pent-4-enamide

To a solution of 2-(3-methoxyphenyl)pent-4-enoic acid (1.5 g, 7.28 mmol) in DCM (80 ml) were added PyBOP (5.68 g, 10.92 mmol) and DIPEA (3.71 ml, 21.84 mmol) under argon atmosphere and the reaction mixture was stirred at 25° C. for 0.5 h. 3-Methoxy-4-oxazol-5-yl-phenylamine (1.66 g, 8.73 mmol) was added to the reaction mixture, and the resulting mixture was allowed to stir at 25° C. for 16 h. The mixture was washed with water, the organic layer was separated and the aqueous layer was extracted with DCM (60 ml). The combined organic layers were dried over anhydrous Na$_2$SO$_4$, filtered, and evaporated off in vacuo. Resulting crude mass was purified by column chromatography over normal silica gel (30-40% EtOAc/hexane) to get N-[3-methoxy-4-(1, 3-oxazol-5-yl) phenyl]-2-(3-methoxyphenyl) pent-4-enamide (2.3 g, 83.47%) as a white solid. LC-MS: 379.4 (M+H)$^+$.

Step 3: 4,5-Dihydroxy-N-(3-methoxy-4-oxazol-5-yl-phenyl)-2-(3-methoxyphenyl)pentanamide To a solution of N-[3-methoxy-4-(1,3-oxazol-5-yl)phenyl]-2-(3-methoxyphenyl)pent-4-enamide (2.3 g, 6.08 mmol) and NMO (1.42 g, 12.16 mmol) in acetone (100 ml) and water (16.6 ml) at 25° C. was added OsO$_4$ (4% in water; 0.15 ml), and the resulting mixture was stirred at 25° C. for 16 h. Saturated aqueous sodium thiosulfate solution (60 ml) was added to the reaction mixture and extracted with EtOAc (2×150 ml). The combined organic layer were dried over anhydrous Na$_2$SO$_4$, filtered, and concentrated in vacuo. The resulting crude mass was purified by column chromatography over normal silica gel (70-80% EtOAc/hexane) to get 4, 5-dihydroxy-N-[3-methoxy-4-(1, 3-oxazol-5-yl) phenyl]-2-(3-methoxyphenyl) pentanamide (1.89 g, 75.31%) as a yellow solid. LC-MS: 413.1 (M+H)$^+$.

Step 4: 5-Hydroxy-1-(3-methoxy-4-oxazol-5-yl-phenyl)-3-(3-methoxyphenyl)pyrrolidin-2-one To a solution of 4, 5-dihydroxy-N-[3-methoxy-4-(1, 3-oxazol-5-yl) phenyl]-2-(3-methoxyphenyl) pentanamide (1.89 g, 4.58 mmol) in THF (90 ml) was added a solution of NaIO$_4$ (1.95 g, 9.17 mmol) in water (42 ml), and the resulting mixture was stirred at 25° C. for 2 h. The reaction mixture was quenched using saturated aqueous Na$_2$S$_2$O$_3$ solution, and extracted with EtOAc (2×100 ml). The combined organic layers were washed with water, dried over anhydrous Na$_2$SO$_4$, filtered, and evaporated off in vacuo to get 5-hydroxy-1-[3-methoxy-4-(1, 3-oxazol-5-yl) phenyl]-3-(3-methoxyphenyl) pyrrolidin-2-one (1.63 g) as white solid that was used in the next step without any further purification. LC-MS: 381.2 (M+H)$^+$.

Step 5: 1-(3-Methoxy-4-oxazol-5-yl-phenyl)-3-phenyl-pyrrolidin-2-one

To a solution of 5-hydroxy-1-[3-methoxy-4-(1, 3-oxazol-5-yl) phenyl]-3-(3-methoxyphenyl) pyrrolidin-2-one (1.63 g, 4.28 mmol) in DCM (150 ml) at 0° C. were added Et$_3$SiH (8 ml) and TFA (8 ml), and the reaction mixture was stirred at 25° C. for 2 h. Volatilities were removed in vacuo. The resultant residue was diluted with DCM (120 ml) and washed with saturated aqueous NaHCO$_3$ solution. The organic layer was dried over anhydrous Na$_2$SO$_4$, filtered, and evaporated off under reduced pressure. The resulting crude mass was purified by column chromatography over normal silica gel (50% EtOAc/hexane) to get 1-[3-methoxy-4-(1, 3-oxazol-5-yl) phenyl]-3-(3-methoxyphenyl) pyrrolidin-2-one (950 mg, 56.92% from Step 3) as off white solid. LC-MS: 365.3 (M+H)$^+$.

Example 4

3-(2-Chlorophenyl)-1-(3-methoxy-4-oxazol-5-yl-phenyl)pyrrolidin-2-one

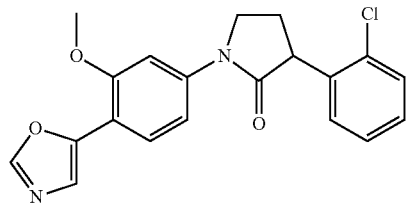 [SMILES: COc1cc(N2CCC(c3ccccc3Cl)C2=O)ccc1-c1cnco1]

The title compound was prepared in analogy to Example 3, using 2-chlorobenzeneacetic acid in Step 1. LC-MS: 369.0 (M+H)$^+$.

Example 5

1-Benzyl-3-[3-methoxy-4-(1H-pyrazol-4-yl)phenyl]hexahydropyrimidin-2-one

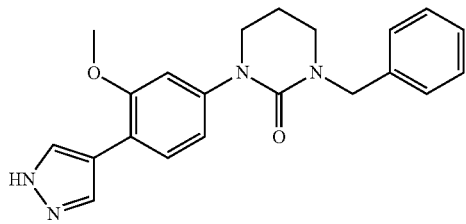 [SMILES: COc1cc(N2CCCN(Cc3ccccc3)C2=O)ccc1-c1cn[nH]c1]

Step 1: Benzyl N-{3-[(4-bromo-3-methoxyphenyl)amino] propyl} carbamate

To a solution of 4-bromo-3-methoxy-phenylamine (2 g, 9.90 mmol) in DCM (100 ml) at 0° C. were added 3-[(benzyloxycarbonyl) amino] propionaldehyde (2.46 g, 11.88 mmol) and AcOH (0.57 ml, 9.90 mmol), and the resulting reaction mixture was stirred at 0° C. for 0.5 h. Then NaBH(OAc)$_3$ (3.14 g, 14.85 mmol) was added to the reaction mixture that was again stirred at 25° C. for 12 h. The mixture was diluted with water (40 ml), the organic layer was separated and the aqueous layer was re-extracted with DCM (2×40 ml). The combined organic layers were evaporated off in vacuo. The resulting crude material was purified by column chromatography over normal silica gel (25-30% EtOAc/hexane) to get benzyl N-{3-[(4-bromo-3-methoxyphenyl) amino] propyl} carbamate (1.4 g, 36.21%) as a yellow sticky solid LC-MS: 395.2 (M+H)$^+$.

Step 2: 1-(4-Bromo-3-methoxyphenyl)-1,3-diazinan-2-one

To a solution of KOtBu (799 mg, 7.12 mmol) in THF (30 ml) at 0° C. was added a solution of benzyl N-{3-[(4-bromo-3-methoxyphenyl)amino]propyl} carbamate (1.4 g, 3.56 mmol) in THF (30 ml), and the resulting mixture was stirred at 25° C. for 12 h. The mixture was quenched with saturated aqueous ammonium chloride solution and extracted with EtOAc (2×80 ml). The combined organic layers were dried over anhydrous Na$_2$SO$_4$, filtered, and evaporated off in vacuo. The resulting residue was triturated using 30% EtOAc/hexane to get 1-(4-bromo-3-methoxyphenyl)-1,3-diazinan-2-one (667 mg, 65.67%) as a yellow solid. LC-MS: 284.8 (M+H)$^+$.

Step 3: 1-Benzyl-3-(4-bromo-3-methoxyphenyl)-1,3-diazinan-2-one

To a suspension of NaH (60% in mineral oil) (31.57 mg, 0.78 mmol) in DMF (2 ml) at 0° C. was added a solution of 1-(4-bromo-3-methoxyphenyl)-1, 3-diazinan-2-one (150 mg, 0.52 mmol) in DMF (5 ml), and the resulting mixture was stirred at 0° C. for 0.5 h. Then benzyl bromide (0.094 ml, 0.78 mmol) was added to the mixture that was allowed to stir at 25° C. for another 12 h. The mixture was diluted with water (15 ml) and extracted with EtOAc (2×40 ml). The combined organic layers were dried over anhydrous Na$_2$SO$_4$, filtered, and evaporated off in vacuo to get 1-benzyl-3-(4-bromo-3-methoxyphenyl)-1,3-diazinan-2-one (244 mg, crude) as a light yellow sticky solid that was used in the next step without any further purification.

LC-MS: 374.8 (M+H)$^+$.

Step 4: 1-Benzyl-3-[3-methoxy-4-(1H-pyrazol-4-yl)phenyl]hexahydropyrimidin-2-one To a solution of 1-benzyl-3-(4-bromo-3-methoxyphenyl)-1,3-diazinan-2-one (240 mg, 0.64 mmol) in dioxane (16 ml) and water (4 ml) was added K$_2$CO$_3$ (265 mg, 1.92 mmol). The mixture was purged with argon for 10 min. To this mixture were then added [1-(tert-butoxycarbonyl)-1H-pyrazol-4-yl]boronic acid pinacol ester (282 mg, 0.96 mmol) and Pd(dppf)$_2$Cl$_2$.DCM (20.90 mg, 0.02 mmol), purged again with argon for another 10 min, and then allowed to heat at 80° C. for 16 h. The mixture was diluted with water, and extracted with EtOAc (2×30 ml). The combined organic layers were dried over anhydrous Na$_2$SO$_4$, filtered, and evaporated off in vacuo. The resulting crude material was purified by column chromatography over normal silica gel (55-65% EtOAc/hexane) to get 1-benzyl-3-[3-methoxy-4-(1H-pyrazol-4-yl) phenyl]-1,3-diazinan-2-one (44 mg, 23.09% from 4) as an off-white solid. LC-MS: 363.0 (M+H)$^+$.

Example 6

1-[(2-Chlorophenyl)methyl]-3-[3-methoxy-4-(1H-pyrazol-4-yl)phenyl]hexahydropyrimidin-2-one

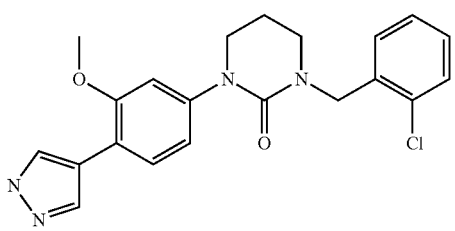 [SMILES: COc1cc(N2CCCN(Cc3ccccc3Cl)C2=O)ccc1-c1cn[nH]c1]

The title compound was prepared in analogy to Example 5, using 1-(bromomethyl)-2-chloro-benzene in Step 3. LC-MS: 397.0 (M+H)$^+$.

Example 7

1-[(3-Methoxyphenyl)methyl]-3-[3-methoxy-4-(1H-pyrazol-4-yl)phenyl]hexahydropyrimidin-2-one

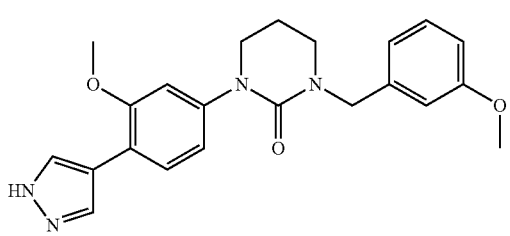 [SMILES: COc1cccc(CN2CCCN(c3ccc(-c4cn[nH]c4)c(OC)c3)C2=O)c1]

The title compound was prepared in analogy to Example 5, using 1-(bromomethyl)-3-methoxy-benzene in Step 3. LC-MS: 393.0 (M+H)+.

Example 8

1-(3-Methoxy-4-oxazol-5-yl-phenyl)-3-phenyl-pyrrolidin-2-one

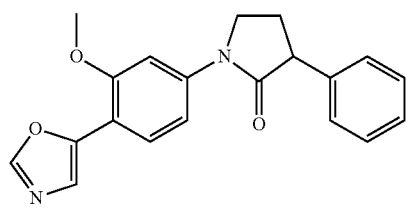 [SMILES: COc1cc(N2CCC(c3ccccc3)C2=O)ccc1-c1cnco1]

The title compound was prepared in analogy to Example 3, using phenyl acetic acid in Step 1. LC-MS: 335.0 (M+H)+.

Example 9

1-Benzyl-3-[3-methoxy-4-(1H-pyrazol-4-yl)phenyl]imidazolidin-2-one

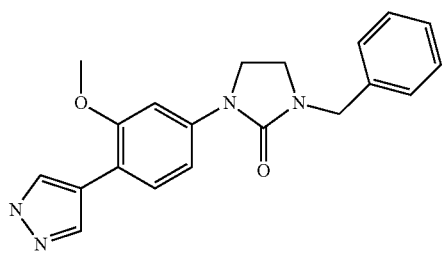 [SMILES: COc1cc(N2CCN(Cc3ccccc3)C2=O)ccc1-c1cn[nH]c1]

The title compound was prepared in analogy to Example 5, using tert-butyl N-(2-oxoethyl)carbamate in Step 1. LC-MS: 349.0 (M+H)+.

Example 10

1-[(2-Chlorophenyl)methyl]-3-[3-methoxy-4-(1H-pyrazol-4-yl)phenyl]imidazolidin-2-one

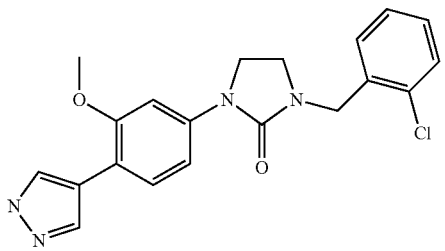 [SMILES: COc1cc(N2CCN(Cc3ccccc3Cl)C2=O)ccc1-c1cn[nH]c1]

The title compound was prepared in analogy to Example 5, using tert-butyl N-(2-oxoethyl)carbamate in Step 1 and 1-(bromomethyl)-2-chloro-benzene in Step 3. LC-MS: 383.0 (M+H)+.

Example 11

1-[(3-Methoxyphenyl)methyl]-3-[3-methoxy-4-(1H-pyrazol-4-yl)phenyl]imidazolidin-2-one

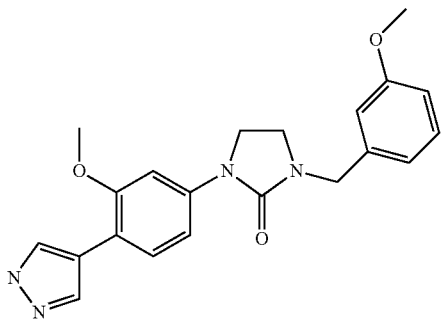 [SMILES: COc1cccc(CN2CCN(c3ccc(-c4cn[nH]c4)c(OC)c3)C2=O)c1]

The title compound was prepared in analogy to Example 5, using tert-butyl N-(2-oxoethyl)carbamate in Step 1 and 1-(bromomethyl)-3-methoxy-benzene in Step 3. LC-MS: 379.0 (M+H)+.

Example 12

1-[3-Methoxy-4-(1H-pyrazol-4-yl)phenyl]-3-phenyl-pyrrolidin-2-one

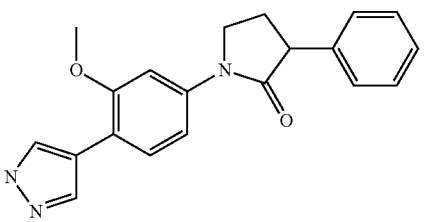 [SMILES: COc1cc(N2CCC(c3ccccc3)C2=O)ccc1-c1cn[nH]c1]

Step 1: 2-Phenylpent-4-enoic acid

To a solution of phenyl acetic acid (2 g, 14.7 mmol) in THF (60 ml) at −78° C. was added LiHMDS (1M solution in THF) (32.35 ml, 32.35 mmol), and the reaction mixture was stirred at −78° C. for 0.5 h. Allyl iodide (1.34 ml, 14.7 mmol) was added to the reaction mixture at −78° C., and the mixture was slowly allowed to warm to 25° C. over a period of 3 h. It was quenched with saturated aqueous ammonium chloride solution, acidified using 1N aqueous HCl solution and extracted with EtOAc (2×80 ml). The combined organic layers were dried over anhydrous $Na_2SO_4$, filtered, and concentrated under reduced pressure. The resulting crude material was purified by column chromatography over normal silica gel (10-20% EtOAc/hexane) to get 2-phenylpent-4-enoic acid (2.26 g, 87.21%) as light yellow oil. LC-MS: 175.2 (M−H$^+$).

Step 2: N-(4-Bromo-3-methoxyphenyl)-2-phenylpent-4-enamide

To a solution of 2-phenylpent-4-enoic acid (1.5 g, 8.52 mmol) in DCM (30 ml) at 0° C. was added oxalyl chloride (1.10 ml, 12.78 mmol), and the mixture was stirred at 25° C. for 3 h. Volatilities were removed in vacuo. Resulting acid chloride was dissolved in DCM (10 ml) and added to a solution of 4-bromo-3-methoxyaniline (1.71 g, 8.50 mmol) and $Et_3N$ (2.37 ml, 8.50 mmol) in DCM (20 ml) at 0° C. Reaction mixture was stirred at 25° C. for 16 h. Solvent was evaporated off in vacuo, and resulting crude material was purified by column chromatography over normal silica gel (10-15% EtOAc/hexane) to get N-(4-bromo-3-methoxyphenyl)-2-phenylpent-4-enamide (1.9 g, 62.01%) as yellow sticky solid. LC-MS: 359.8 (M+H$^+$).

Step 3: N-(4-Bromo-3-methoxyphenyl)-4,5-dihydroxy-2-phenylpentanamide

To a solution of N-(4-bromo-3-methoxyphenyl)-2-phenylpent-4-enamide (1 g, 2.77 mmol) and NMO (976 mg, 8.33 mmol) in acetone (35 ml) and water (4.5 ml) at 25° C. was added $OsO_4$ (4% in water) (0.144 ml), and the mixture was stirred at 25° C. for 12 h. It was quenched with 1N aqueous sodium thiosulfate solution (20 ml), and extracted with EtOAc (2×80 ml). Combined organic layers were dried over anhydrous $Na_2SO_4$, filtered, and concentrated in vacuo. Resulting crude material was purified by column chromatography over normal silica gel (70% EtOAc/hexane) to get N-(4-bromo-3-methoxyphenyl)-4,5-dihydroxy-2-phenylpentanamide (538 mg, 49.12%) as white solid. LC-MS: 394.2 (M+H$^+$).

Step 4: 1-(4-Bromo-3-methoxyphenyl)-5-hydroxy-3-phenylpyrrolidin-2-one

To a solution of N-(4-bromo-3-methoxyphenyl)-4,5-dihydroxy-2-phenylpentanamide (535 mg, 1.35 mmol) in THF (25 ml) was added a solution of $NaIO_4$ (578 mg, 2.71 mmol) in water (12 ml), and the resulting mixture was stirred at 25° C. for 2 h. It was quenched with saturated aqueous $Na_2S_2O_4$ solution and extracted with EtOAc (2×40 ml). Combined organic layers were washed with water, dried over anhydrous $Na_2SO_4$, filtered, and evaporated off in vacuo to get 1-(4-bromo-3-methoxyphenyl)-5-hydroxy-3-phenylpyrrolidin-2-one (479 mg, 97.39%) as off-white solid that was used in the next step with out any further purification. LC-MS: 362.0 (M+H$^+$).

Step 5: 1-(4-Bromo-3-methoxyphenyl)-3-phenylpyrrolidin-2-one

To a solution of 1-(4-bromo-3-methoxyphenyl)-5-hydroxy-3-phenylpyrrolidin-2-one (475 mg, 1.31 mmol) in DCM (15 ml) at 0° C. were added $Et_3SiH$ (2.2 ml) and TFA (2.2 ml), and the resulting mixture was stirred at 25° C. for 2 h. Volatilities were removed in vacuo. The obtained residue was diluted with DCM (50 ml) and washed with saturated aqueous $NaHCO_3$ solution. Organic layers were dried over anhydrous $Na_2SO_4$, filtered, and evaporated off in vacuo. Resulting crude mass was purified by column chromatography over normal silica gel (20-25% EtOAc/hexane) to get 1-(4-bromo-3-methoxyphenyl)-3-phenylpyrrolidin-2-one (345 mg, 75.94%) as off white solid. LC-MS: 345.8 (M+H$^+$).

Step 6: 1-[3-Methoxy-4-(1H-pyrazol-4-yl) phenyl]-3-phenylpyrrolidin-2-one

To a solution of 1-(4-bromo-3-methoxyphenyl)-3-phenylpyrrolidin-2-one (342 mg, 0.98 mmol) in dioxane (10 ml) and water (4 ml) was added $K_2CO_3$ (410 mg, 1.48 mmol). The mixture was purged with argon for 10 min. Then [1-(tert-butoxycarbonyl)-1H-pyrazol-4-yl]boronic acid pinacol ester (436 mg, 1.48 mmol) and $Pd(dppf)_2Cl_2$*DCM (32.28 mg, 0.04 mmol) were added to the reaction mixture, and purged again with argon for another 10 min. Reaction mixture was heated at 80° C. for 16 h. The mixture was diluted with water, and extracted with EtOAc (2×40 ml). Combined organic layers were dried over anhydrous $Na_2SO_4$, filtered, and evaporated off in vacuo. Resulting crude mass was purified by column chromatography over normal silica gel (55-65% EtOAc/hexane) to get 1-[3-methoxy-4-(1H-pyrazol-4-yl) phenyl]-3-phenylpyrrolidin-2-one (80 mg, 24.28%) as off-white solid. LC-MS: 334.0 (M+H$^+$).

Example 13

3-Phenyl-1-[4-(1H-pyrazol-4-yl)phenyl]pyrrolidin-2-one

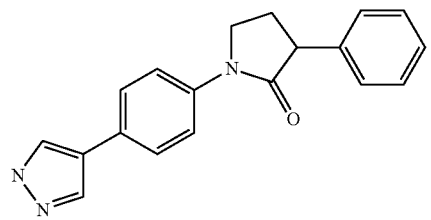 [SMILES: O=C1C(c2ccccc2)CCN1c1ccc(-c2cn[nH]c2)cc1]

The title compound was prepared in analogy to Example 12, using 4-bromoaniline in Step 2. LC-MS: 304.0 (M+H$^+$)$^+$.

Example 14

3-(3-Methoxyphenyl)-1-[4-(1H-pyrazol-4-yl)phenyl]pyrrolidin-2-one

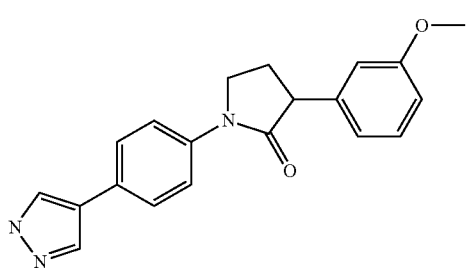 [SMILES: COc1cccc(C2CCN(c3ccc(-c4cn[nH]c4)cc3)C2=O)c1]

The title compound was prepared in analogy to Example 12, using 3-methylphenyl acetic acid in step 1, and 4-bromoaniline in Step 2. LC-MS: 334.2 (M+H)$^+$.

Example 15

3-(4-Chlorophenyl)-1-[4-(1H-pyrazol-4-yl)phenyl]pyrrolidin-2-one

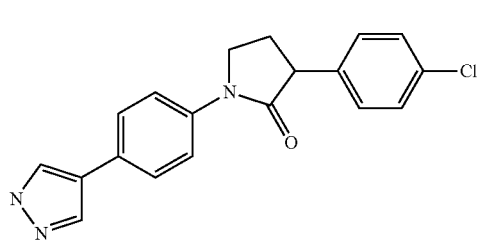 [SMILES: O=C1C(c2ccc(Cl)cc2)CCN1c1ccc(-c2cn[nH]c2)cc1]

The title compound was prepared in analogy to Example 12, using 4-chlorophenyl acetic acid in step 1, and 4-bromoaniline in Step 2. LC-MS: 338.2 (M+H)$^+$.

Example 16

3-(4-Fluorophenyl)-1-[4-(1H-pyrazol-4-yl)phenyl]pyrrolidin-2-one

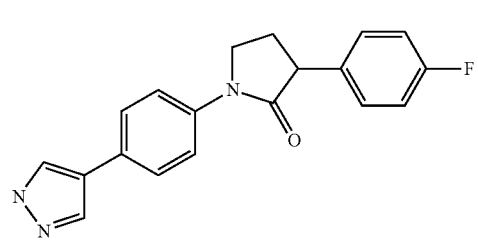 [SMILES: O=C1C(c2ccc(F)cc2)CCN1c1ccc(-c2cn[nH]c2)cc1]

The title compound was prepared in analogy to Example 12, using 4-fluorophenyl acetic acid in step 1, and 4-bromoaniline in Step 2. LC-MS: 322.0 (M+H)$^+$.

Example 17

3-(3-Chlorophenyl)-1-[4-(1H-pyrazol-4-yl)phenyl]pyrrolidin-2-one

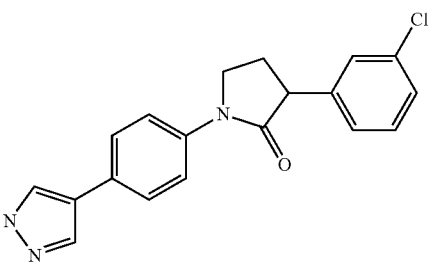 [SMILES: O=C1C(c2cccc(Cl)c2)CCN1c1ccc(-c2cn[nH]c2)cc1]

The title compound was prepared in analogy to Example 12, using 3-chlorophenyl acetic acid in step 1, and 4-bromoaniline in Step 2. LC-MS: 338.2 (M+H)$^+$.

Example 18

1-[(3-Chlorophenyl)methyl]-3-[3-methoxy-4-(1H-pyrazol-4-yl)phenyl]imidazolidin-2-one

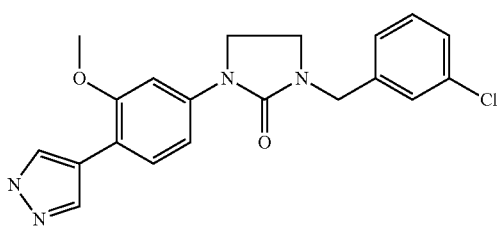 [SMILES: COc1cc(N2CCN(Cc3cccc(Cl)c3)C2=O)ccc1-c1cn[nH]c1]

The title compound was prepared in analogy to Example 5, using tert-butyl N-(2-oxoethyl)carbamate in Step 1, and 1-(bromomethyl)-3-chloro-benzene in Step 3. LC-MS: 383.0 (M+H)$^+$.

Example 19

1-[(3-Fluorophenyl)methyl]-3-[3-methoxy-4-(1H-pyrazol-4-yl)phenyl]imidazolidin-2-one

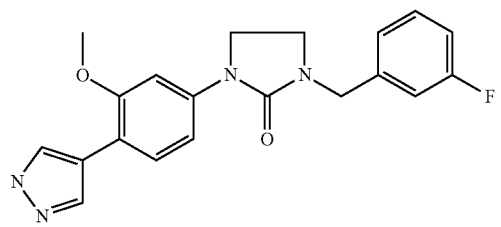 [SMILES: COc1cc(N2CCN(Cc3cccc(F)c3)C2=O)ccc1-c1cn[nH]c1]

The title compound was prepared in analogy to Example 5, using tert-butyl N-(2-oxoethyl)carbamate in Step 1, and 1-(bromomethyl)-3-fluoro-benzene in Step 3. LC-MS: 366.9 (M+H)$^+$.

Example 20

1-[3-Methoxy-4-(1H-pyrazol-4-yl)phenyl]-3-[[3-(trifluoromethyl)phenyl]methyl]imidazolidin-2-one

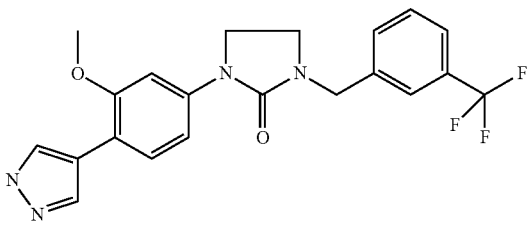 [SMILES: COc1cc(N2CCN(Cc3cccc(C(F)(F)F)c3)C2=O)ccc1-c1cn[nH]c1]

The title compound was prepared in analogy to Example 5, using tert-butyl N-(2-oxoethyl)carbamate in Step 1, and 1-(bromomethyl)-3-trifluoromethyl-benzene in Step 3. LC-MS: 417.0 (M+H)$^+$.

Example 21

1-[3-Methoxy-4-(1H-pyrazol-4-yl)phenyl]-3-[[3-(trifluoromethoxy)phenyl]methyl]imidazolidin-2-one

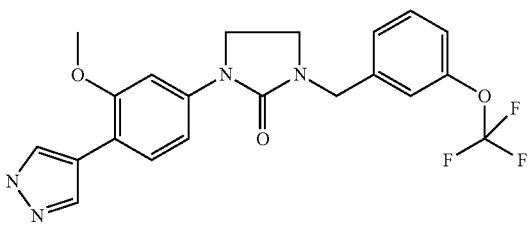 [SMILES: COc1cc(N2CCN(Cc3cccc(OC(F)(F)F)c3)C2=O)ccc1-c1cn[nH]c1]

The title compound was prepared in analogy to Example 5, using tert-butyl N-(2-oxoethyl)carbamate in Step 1, and 1-(bromomethyl)-3-trifluoromethoxy-benzene in Step 3. LC-MS: 433.1 (M+H)$^+$.

Example 22

1-[(3-Ethoxyphenyl)methyl]-3-[3-methoxy-4-(1H-pyrazol-4-yl)phenyl]imidazolidin-2-one

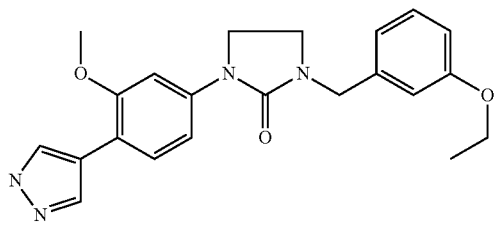

The title compound was prepared in analogy to Example 5, using tert-butyl N-(2-oxoethyl)carbamate in Step 1, and 1-(bromomethyl)-3-ethoxy-benzene in Step 3. LC-MS: 393.0 (M+H)$^+$.

Example 23

3-Benzyl-1-(3-methoxy-4-(1H-pyrazol-4-yl)phenyl)pyrrolidin-2-one

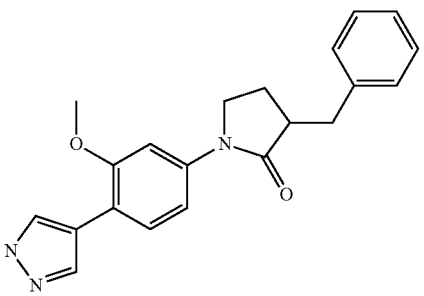 [SMILES: COc1cc(N2CCC(Cc3ccccc3)C2=O)ccc1-c1cn[nH]c1]

Step 1: 1-(4-Bromo-3-methoxyphenyl)pyrrolidin-2-one

Under an atmosphere of nitrogen, in a 100 mL round-bottomed flask at 0° C., 4-bromo-3-methoxyaniline (2 g, 9.9 mmol) and KOH (6.93 ml, 13.9 mmol) were combined with dichloromethane (30 ml) to give a light brown solution. Then 4-bromobutanoyl chloride (1.84 g, 1.15 ml, 9.9 mmol) was added. The reaction was stirred for 1 h at RT. The reaction mixture was poured into 50 ml dichloromethane and extracted with water (3×20 ml). The organic layer was dried over Na$_2$SO$_4$ and concentrated in vacuo.

The residue was dissolved in 30 ml dichloromethane. Then tetrabutylammonium bromide (63.8 mg, 198 µmol) and KOH (50%, 6 ml) were added. The reaction was stirred for 1 h at RT. The reaction mixture was poured into dichloromethane (50 ml) and extracted with water (3×20 ml). The organic layers were dried over Na$_2$SO$_4$ and concentrated in vacuo. The crude material was purified by flash chromatography (silica gel, 50 g, 20% to 50% EtOAc in heptane). The title compound was obtained as a off-white crystalline (1.92 g, 71.8%). MS (m/e)=272.1 [M+H]$^+$.

Step 2: 3-Benzyl-1-(4-bromo-3-methoxyphenyl)pyrrolidin-2-one

Under an atmosphere of nitrogen, in a 25 mL three-necked flask, 2,2,6,6-tetramethylpiperidine (188 mg, 1.33 mmol) was combined with THF (4 ml) to give a colorless solution. At 0° C., n-butyllithium (1.6 M in hexane, 833 µl, 1.33 mmol) was added slowly. The reaction was stirred for 30 min at 0° C. Then 1-(4-bromo-3-methoxyphenyl)pyrrolidin-2-one (300 mg, 1.11 mmol, Eq: 1.00) diluted in 3 ml THF was added slowly. The reaction was stirred for 1 h at 0° C. Then (bromomethyl)benzene (228 mg, 159 µl, 1.33 mmol) was added. The reaction was stirred for 30 min at 0° C. The reaction was stirred for 5 d at RT. The reaction mixture was poured into 2×20 mL ethyl acetate and extracted with water (2×15 ml). The organic layer was washed with 15 ml brine. The organic layer was dried over Na$_2$SO$_4$ and concentrated in vacuo. The crude material was purified by flash chromatography (silica gel, 20 g, 0% to 20% EtOAc in heptane). The title compound was obtained as a light yellow gum (120 mg, 30.0%). MS (m/e)=360.06 [M+H]$^+$.

Step 3: 3-Benzyl-1-(3-methoxy-4-(1H-pyrazol-4-yl)phenyl)pyrrolidin-2-one

3-Benzyl-1-(4-bromo-3-methoxyphenyl)pyrrolidin-2-one (120 mg, 333 mol), tert-butyl 4-(4,4,5,5-tetramethyl-1,3,2- dioxaborolan-2-yl)-1H-pyrazole-1-carboxylate (108 mg, 366 μmol) and sodium carbonate (833 μl, 1.67 mmol) were combined with dioxane (5.00 ml). Under an atmosphere of nitrogen, 1,1'-bis(diphenylphosphino)ferrocene-palladium (II)dichloride dichloromethane complex (27.2 mg, 33.3 mol) was added. The reaction mixture was stirred overnight at 80° C. The reaction mixture was poured into 25 mL ethyl acetate and extracted with water (2×15 mL). The organic layer was dried over $Na_2SO_4$ and concentrated in vacuo. The crude material was purified by flash chromatography (silica gel, 10 g, 30% to 60% EtOAc in heptane). The title compound was obtained as a light brown solid (7.3 mg, 6.31%). MS (m/e)=348.17 $[M+H]^+$.

Example 24

1-(3-Methoxy-4-(1H-pyrazol-4-yl)phenyl)-3-(3-methoxyphenyl)pyrrolidin-2-one

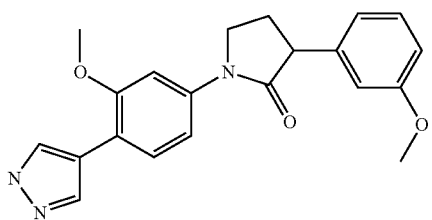 [SMILES: COc1cccc(C2CCN(c3ccc(-c4cn[nH]c4)c(OC)c3)C2=O)c1]

The title compound was prepared in analogy to example 12, using 2-(3-methoxyphenyl)acetic acid in step 1, and 4-bromo-3-methoxyaniline in step 2. MS (m/e)=364.17 $[M+H]^+$.

Example 25

3-(3-Chlorophenyl)-1-(3-methoxy-4-(1H-pyrazol-4-yl)phenyl)pyrrolidin-2-one

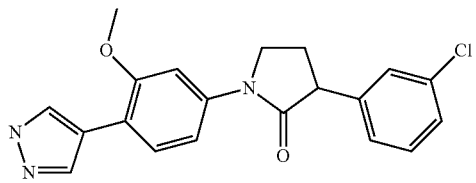 [SMILES: COc1cc(N2CCC(c3cccc(Cl)c3)C2=O)ccc1-c1cn[nH]c1]

The title compound was prepared in analogy to example 12, using 2-(3-chlorophenyl)acetic acid in step 1, and 4-bromo-3-methoxyaniline in step 2. MS (m/e)=368.11 $[M+H]^+$.

Example 26

3-(3-Fluorophenyl)-1-(3-methoxy-4-(1H-pyrazol-4-yl)phenyl)pyrrolidin-2-one

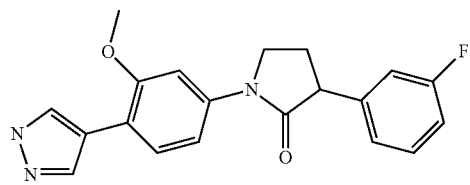 [SMILES: COc1cc(N2CCC(c3cccc(F)c3)C2=O)ccc1-c1cn[nH]c1]

The title compound was prepared in analogy to example 12, using 2-(3-fluorophenyl)acetic acid in step 1, and 4-bromo-3-methoxyaniline in step 2. MS (m/e)=352.14 $[M+H]^+$.

Example 27

1-[(3-Methoxyphenyl)methyl]-3-[4-(1H-pyrazol-4-yl)phenyl]imidazolidin-2-one

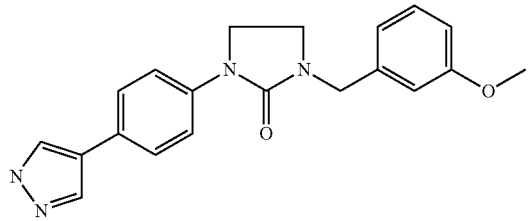 [SMILES: COc1cccc(CN2CCN(c3ccc(-c4cn[nH]c4)cc3)C2=O)c1]

The title compound was prepared in analogy to Example 5, using tert-butyl N-(2-oxoethyl)carbamate and 4-bromophenylamine in Step 1, and 1-(bromomethyl)-3-methoxy-benzene in Step 3. LC-MS: 349 $(M+H)^+$.

Example 28

1-[(3-Methoxyphenyl)methyl]-3-[3-methyl-4-(1H-pyrazol-4-yl)phenyl]imidazolidin-2-one

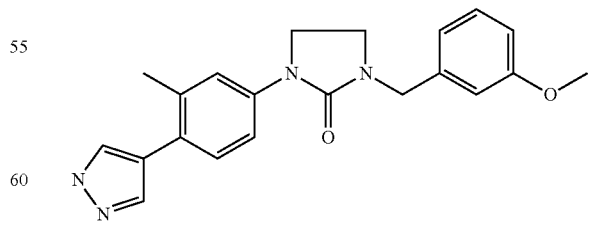

The title compound was prepared in analogy to Example 5, using tert-butyl N-(2-oxoethyl)carbamate and 4-bromo-3-methyl-aniline in Step 1, and 1-(bromomethyl)-3-methoxy-benzene in Step 3. LC-MS: 363 $(M+H)^+$.

Example 29

1-[3-Chloro-4-(1H-pyrazol-4-yl)phenyl]-3-[(3-methoxyphenyl)methyl]imidazolidin-2-one

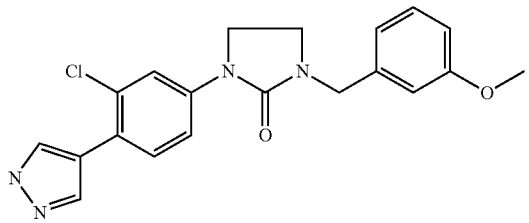 [SMILES: COc1cccc(CN2CCN(c3ccc(-c4cn[nH]c4)c(Cl)c3)C2=O)c1]

The title compound was prepared in analogy to Example 5, using tert-butyl N-(2-oxoethyl)carbamate and 4-bromo-3-chloro-aniline in Step 1, and 1-(bromomethyl)-3-methoxy-benzene in Step 3. LC-MS: 383 (M+H)+.

Example 30

1-[2-Fluoro-4-(1H-pyrazol-4-yl)phenyl]-3-[(3-methoxyphenyl)methyl]imidazolidin-2-one

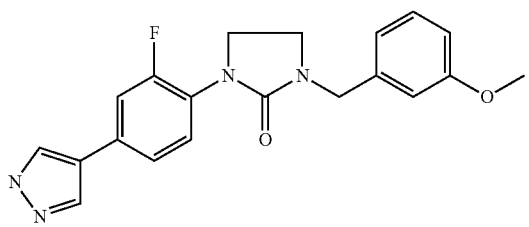 [SMILES: COc1cccc(CN2CCN(c3ccc(-c4cn[nH]c4)cc3F)C2=O)c1]

The title compound was prepared in analogy to Example 5, using tert-butyl N-(2-oxoethyl)carbamate and 4-bromo-2-fluoro-aniline in Step 1, and 1-(bromomethyl)-3-methoxy-benzene in Step 3. LC-MS: 367 (M+H)+.

Example 31

1-[3-Fluoro-4-(1H-pyrazol-4-yl)phenyl]-3-[(3-methoxyphenyl)methyl]imidazolidin-2-one

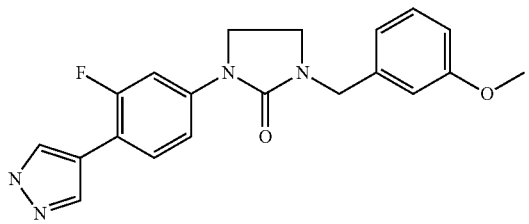 [SMILES: COc1cccc(CN2CCN(c3ccc(-c4cn[nH]c4)c(F)c3)C2=O)c1]

The title compound was prepared in analogy to Example 5, using tert-butyl N-(2-oxoethyl)carbamate and 4-bromo-3-fluoro-aniline in Step 1, and 1-(bromomethyl)-3-methoxy-benzene in Step 3. LC-MS: 367 (M+H)+.

Example 32

1-[3-Ethoxy-4-(1H-pyrazol-4-yl)phenyl]-3-[(3-methoxyphenyl)methyl]imidazolidin-2-one

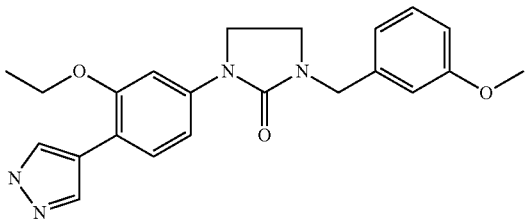 [SMILES: CCOc1cc(N2CCN(Cc3cccc(OC)c3)C2=O)ccc1-c1cn[nH]c1]

The title compound was prepared in analogy to Example 5, using tert-butyl N-(2-oxoethyl)carbamate and 4-bromo-3-ethoxy-aniline in Step 1, and 1-(bromomethyl)-3-methoxy-benzene in Step 3. LC-MS: 393 (M+H)+.

Example 33

1-[(2-Fluorophenyl)methyl]-3-[3-methoxy-4-(1H-pyrazol-4-yl)phenyl]imidazolidin-2-one

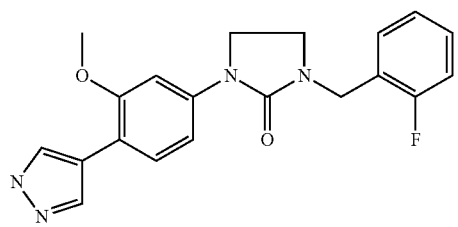 [SMILES: COc1cc(N2CCN(Cc3ccccc3F)C2=O)ccc1-c1cn[nH]c1]

The title compound was prepared in analogy to Example 5, using tert-butyl N-(2-oxoethyl)carbamate in Step 1, and 1-(bromomethyl)-2-fluoro-benzene in Step 3. LC-MS: 367 (M+H)+.

Example 34

1-[3-Methoxy-4-(1H-pyrazol-4-yl)phenyl]-3-(o-tolylmethyl)imidazolidin-2-one

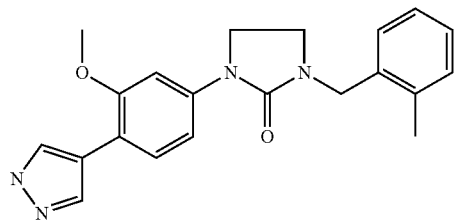

The title compound was prepared in analogy to Example 5, using tert-butyl N-(2-oxoethyl)carbamate in Step 1, and 1-(bromomethyl)-2-methyl-benzene in Step 3. LC-MS: 363 (M+H)+.

Example 35

1-[3-Methoxy-4-(1H-pyrazol-4-yl)phenyl]-3-(m-tolylmethyl)imidazolidin-2-one

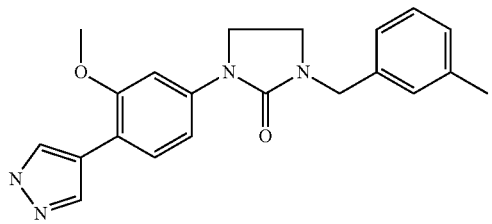 [SMILES: COc1cc(N2CCN(Cc3cccc(C)c3)C2=O)ccc1-c1cn[nH]c1]

The title compound was prepared in analogy to Example 5, using tert-butyl N-(2-oxoethyl)carbamate in Step 1, and 1-(bromomethyl)-3-methyl-benzene in Step 3. LC-MS: 363 (M+H)+.

Example 36

3-[(3-Chlorophenyl)methyl]-1-[3-methoxy-4-(1H-pyrazol-4-yl)phenyl]pyrrolidin-2-one

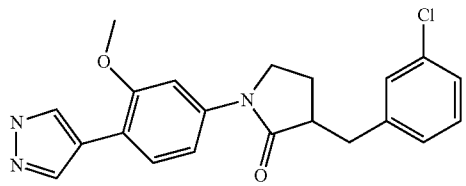 [SMILES: COc1cc(N2CCC(Cc3cccc(Cl)c3)C2=O)ccc1-c1cn[nH]c1]

The title compound was obtained in analogy to example 23, using 1-(bromomethyl)-3-chloro-benzene in step 2. MS: 382.0 (M+H)+.

Example 37

3-[(2-Chlorophenyl)methyl]-1-[3-methoxy-4-(1H-pyrazol-4-yl)phenyl]pyrrolidin-2-one

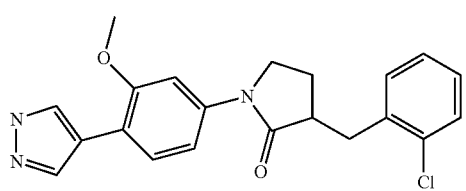 [SMILES: COc1cc(N2CCC(Cc3ccccc3Cl)C2=O)ccc1-c1cn[nH]c1]

The title compound was obtained in analogy to example 23, using 1-(bromomethyl)-2-chloro-benzene in step 2. MS: 382.0 (M+H)+.

Example 38

3-(3-Chlorophenyl)-1-[3-methoxy-4-(1,3-oxazol-5-yl)phenyl]pyrrolidin-2-one

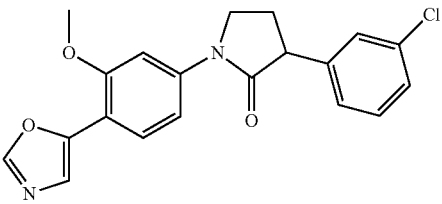 [SMILES: COc1cc(N2CCC(c3cccc(Cl)c3)C2=O)ccc1-c1cnco1]

The title compound was prepared in analogy to Example 3, using 3-chlorophenylacetic acid in step 1. MS: 367.2 (M−H)+.

Example 39

1-[(3-Methoxyphenyl)methyl]-3-[2-methoxy-4-(1H-pyrazol-4-yl)phenyl]imidazolidin-2-one

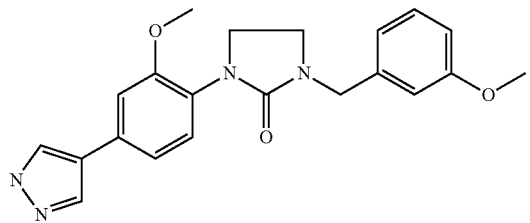 [SMILES: COc1cccc(CN2CCN(c3ccc(-c4cn[nH]c4)cc3OC)C2=O)c1]

The title compound was prepared in analogy to Example 5, using tert-butyl N-(2-oxoethyl)carbamate and 4-bromo-2-methoxy-aniline in Step 1, and 1-(bromomethyl)-3-methoxy-benzene in Step 3. LC-MS: 379 (M+H)+.

Example 40

3-[(3-Methoxyphenyl)methyl]-1-[3-methoxy-4-(1H-pyrazol-4-yl)phenyl]pyrrolidin-2-one

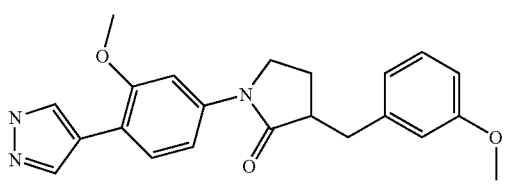 [SMILES: COc1cccc(CC2CCN(c3ccc(-c4cn[nH]c4)c(OC)c3)C2=O)c1]

The title compound was obtained in analogy to example 23, using 1-(bromomethyl)-3-methoxy-benzene in step 2. MS: 378.0 (M+H)+.

Example 41

1-[3-Methoxy-4-(1,3-oxazol-5-yl)phenyl]-3-(2-methoxyphenyl)pyrrolidin-2-one

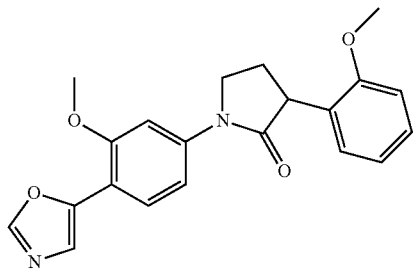 [SMILES: COc1cc(N2CCC(c3ccccc3OC)C2=O)ccc1-c1cnco1]

The title compound was prepared in analogy to Example 3, using 2-methoxyphenylacetic acid in step 1. MS: 365.3 (M+H)+.

Example 42

1-[(2-Methoxyphenyl)methyl]-3-[3-methoxy-4-(1H-pyrazol-4-yl)phenyl]imidazolidin-2-one

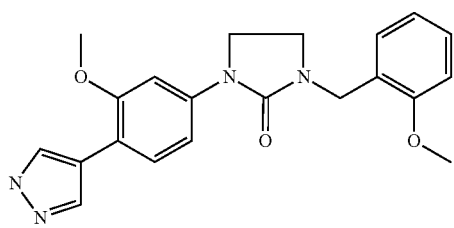 [SMILES: COc1ccccc1CN1CCN(c2ccc(-c3cn[nH]c3)c(OC)c2)C1=O]

The title compound was prepared in analogy to Example 5, using tert-butyl N-(2-oxoethyl)carbamate and in Step 1, and 1-(bromomethyl)-2-methoxy-benzene in Step 3. LC-MS: 379 (M+H)+.

Example 43

1-[3-Methoxy-4-(1H-pyrazol-4-yl)phenyl]-3-(2-phenylethyl)imidazolidin-2-one

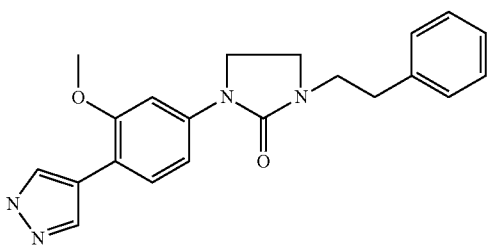 [SMILES: COc1cc(N2CCN(CCc3ccccc3)C2=O)ccc1-c1cn[nH]c1]

The title compound was prepared in analogy to Example 5, using tert-butyl N-(2-oxoethyl)carbamate and in Step 1, and 2-bromoethylbenzene in Step 3. LC-MS: 363 (M+H)+.

Example 44

1-[2-(2-Methoxyphenyl)ethyl]-3-[3-methoxy-4-(1H-pyrazol-4-yl)phenyl]imidazolidin-2-one

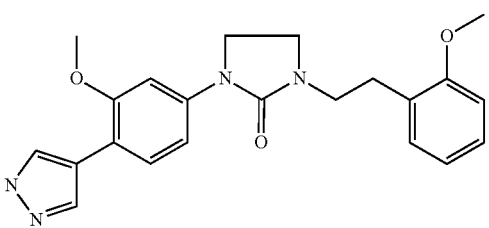 [SMILES: COc1ccccc1CCN1CCN(c2ccc(-c3cn[nH]c3)c(OC)c2)C1=O]

The title compound was prepared in analogy to Example 5, using tert-butyl N-(2-oxoethyl)carbamate and in Step 1, and 1-(2-bromoethyl)-2-methoxy-benzene in Step 3. LC-MS: 393 (M+H)+.

Example 45

1-[2-(2-Chlorophenyl)ethyl]-3-[3-methoxy-4-(1H-pyrazol-4-yl)phenyl]imidazolidin-2-one

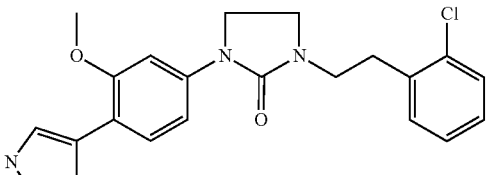

The title compound was prepared in analogy to Example 5, using tert-butyl N-(2-oxoethyl)carbamate and in Step 1, and 1-(2-bromoethyl)-2-chloro-benzene in Step 3. LC-MS: 397 (M+H)+.

Example 46

1-[2-Chloro-4-(1H-pyrazol-4-yl)phenyl]-3-[(3-methoxyphenyl)methyl]imidazolidin-2-one

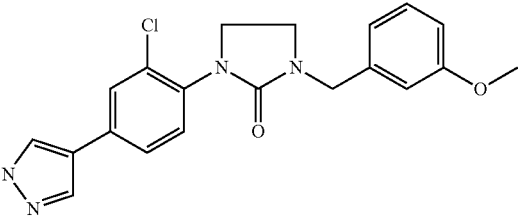

The title compound was prepared in analogy to Example 5, using tert-butyl N-(2-oxoethyl)carbamate and 4-bromo-2-chloro-aniline in Step 1, and 1-(bromomethyl)-3-methoxy-benzene in Step 3. LC-MS: 383 (M+H)+.

Example 47

1-[(4-Fluorophenyl)methyl]-3-[3-methoxy-4-(1H-pyrazol-4-yl)phenyl]imidazolidin-2-one

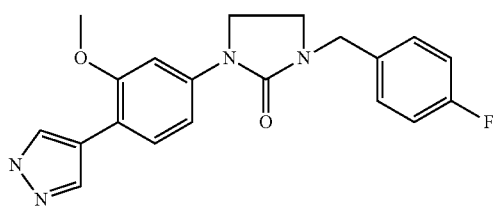 [SMILES: COc1cc(N2CCN(Cc3ccc(F)cc3)C2=O)ccc1-c1cn[nH]c1]

The title compound was prepared in analogy to Example 5, using tert-butyl N-(2-oxoethyl)carbamate in Step 1, and 1-(bromomethyl)-4-fluoro-benzene in Step 3. LC-MS: 367 (M+H)$^+$.

Example 48

1-[3-Methoxy-4-(1H-pyrazol-4-yl)phenyl]-3-(3-pyridylmethyl)imidazolidin-2-one

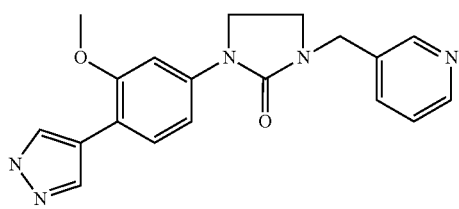 [SMILES: COc1cc(N2CCN(Cc3cccnc3)C2=O)ccc1-c1cn[nH]c1]

The title compound was prepared in analogy to Example 5, using tert-butyl N-(2-oxoethyl)carbamate in Step 1, and 3-(bromomethyl)pyridine in Step 3. LC-MS: 350 (M+H)$^+$.

Example 49

1-[2-(3-Chlorophenyl)ethyl]-3-[3-methoxy-4-(1H-pyrazol-4-yl)phenyl]imidazolidin-2-one

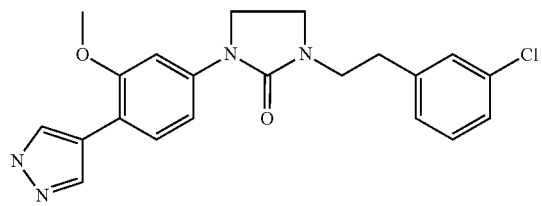 [SMILES: COc1cc(N2CCN(CCc3cccc(Cl)c3)C2=O)ccc1-c1cn[nH]c1]

The title compound was prepared in analogy to Example 5, using tert-butyl N-(2-oxoethyl)carbamate and in Step 1, and 1-(2-bromoethyl)-3-chloro-benzene in Step 3. LC-MS: 397 (M+H)$^+$.

Example 50

1-[2-(4-Chlorophenyl)ethyl]-3-[3-methoxy-4-(1H-pyrazol-4-yl)phenyl]imidazolidin-2-one

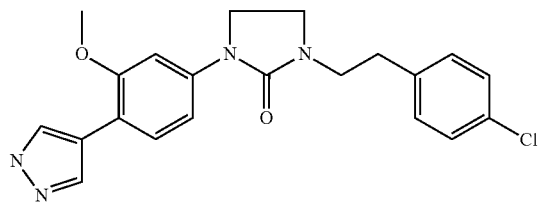 [SMILES: COc1cc(N2CCN(CCc3ccc(Cl)cc3)C2=O)ccc1-c1cn[nH]c1]

The title compound was prepared in analogy to Example 5, using tert-butyl N-(2-oxoethyl)carbamate and in Step 1, and 1-(2-bromoethyl)-4-chloro-benzene in Step 3. LC-MS: 397 (M+H)$^+$.

Example 51

1-[3-Methoxy-4-(1H-pyrazol-4-yl)phenyl]-3-(1-phenylpropyl)imidazolidin-2-one

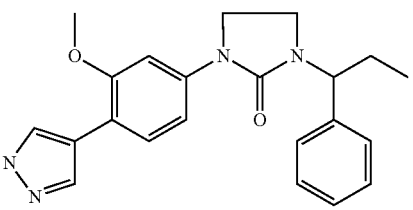 [SMILES: CCC(c1ccccc1)N1CCN(c2ccc(-c3cn[nH]c3)c(OC)c2)C1=O]

The title compound was prepared in analogy to example 5, using 1-(4-bromo-3-methoxyphenyl)-3-(1-phenyl-propyl)-imidazolidin-2-one and 4-(4,4,5,5-tetramethyl-[1,3,2]dioxaborolan-2-yl)-pyrazole-1-carboxylic acid tert-butyl ester in Step 4. LC-MS: 377 (M+H)$^+$.

Example 52

3-(3-Methoxyphenyl)-1-[4-(1,3-oxazol-5-yl)phenyl]pyrrolidin-2-one

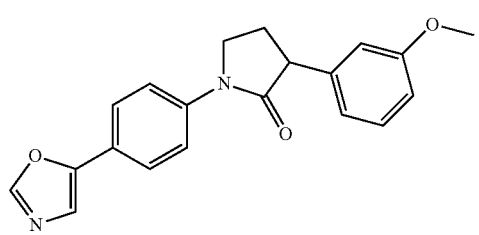 [SMILES: COc1cccc(C2CCN(c3ccc(-c4cnco4)cc3)C2=O)c1]

The title compound was prepared in analogy to Example 3, using 3-methoxyphenylacetic acid in step 1, and 4-oxazol-5-ylaniline in step 2. MS: 335.3 (M+H)$^+$.

Example 53

1-[4-(1,3-Oxazol-5-yl)phenyl]-3-phenylpyrrolidin-2-one

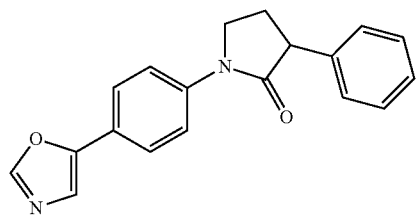 [SMILES: O=C1C(c2ccccc2)CCN1c1ccc(-c2cnco2)cc1]

The title compound was prepared in analogy to Example 3, using phenylacetic acid in step 1, and 4-oxazol-5-ylaniline in step 2. MS: 305.2 (M+H)$^+$.

Example 54

1-[3-Methoxy-4-(4-pyridyl)phenyl]-3-[[2-(trifluoromethyl)phenyl]methyl]imidazolidin-2-one

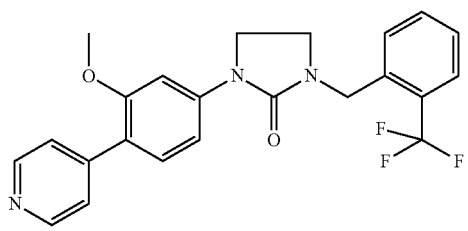 [SMILES: COc1cc(N2CCN(Cc3ccccc3C(F)(F)F)C2=O)ccc1-c1ccncc1]

The title compound was prepared in analogy to Example 5, using tert-butyl N-(2-oxoethyl)carbamate in Step 1, 1-(bromomethyl)-2-trifluoromethyl-benzene in Step 3, and pyridin-4-ylboronic acid in Step 4. LC-MS: 428 (M+H)$^+$.

Example 55

1-[3-Methoxy-4-(4-pyridyl)phenyl]-3-(4-pyridylmethyl)imidazolidin-2-one

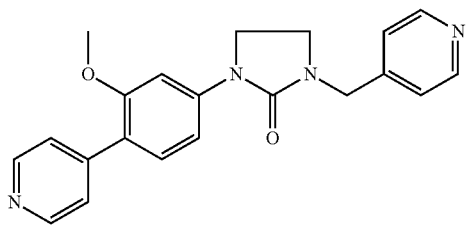 [SMILES: COc1cc(N2CCN(Cc3ccncc3)C2=O)ccc1-c1ccncc1]

The title compound was prepared in analogy to Example 5, using tert-butyl N-(2-oxoethyl)carbamate in Step 1 4-(bromomethyl)pyridine in Step 3, and pyridin-4-ylboronic acid in Step 4. LC-MS: 361 (M+H)$^+$.

Example 56

1-[3-Methoxy-4-(1,3-oxazol-5-yl)phenyl]-3-[3-(trifluoromethyl)phenyl]pyrrolidin-2-one

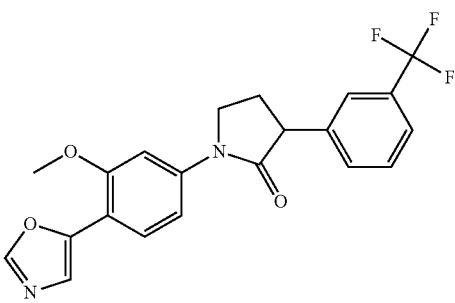 [SMILES: COc1cc(N2CCC(c3cccc(C(F)(F)F)c3)C2=O)ccc1-c1cnco1]

The title compound was prepared in analogy to Example 3, using 3-trifluoromethylphenylacetic acid in step 1. MS: 403.2 (M+H)$^+$.

Example 57

3-(2-Fluorophenyl)-1-[4-(1,3-oxazol-5-yl)phenyl]pyrrolidin-2-one

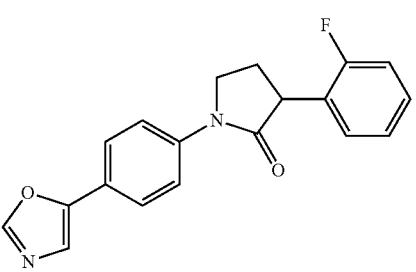 [SMILES: O=C1C(c2ccccc2F)CCN1c1ccc(-c2cnco2)cc1]

The title compound was prepared in analogy to Example 3, using 2-fluorophenylacetic acid in step 1, and 4-oxazol-5-ylaniline in step 2. MS: 323.2 (M+H)$^+$.

Example 58

3-(2-Fluorophenyl)-1-[3-methoxy-4-(1,3-oxazol-5-yl)phenyl]pyrrolidin-2-one

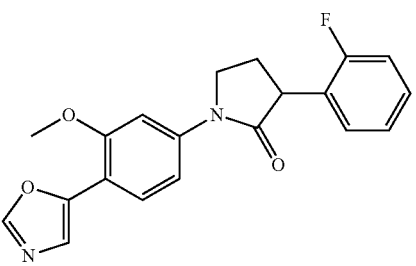 [SMILES: COc1cc(N2CCC(c3ccccc3F)C2=O)ccc1-c1cnco1]

The title compound was prepared in analogy to Example 3, using 2-fluorophenylacetic acid in step 1. MS: 353.2 (M+H)$^+$.

Example 59

1-[(3-Methoxyphenyl)methyl]-3-[4-(1,3-oxazol-5-yl)phenyl]imidazolidin-2-one

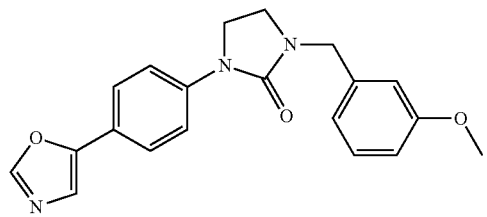 [SMILES: COc1cccc(CN2CCN(c3ccc(-c4cnco4)cc3)C2=O)c1]

Step 1: tert-Butyl 2-(4-(oxazol-5-yl)phenylamino)ethylcarbamate

To a solution of 4-(oxazol-5-yl)aniline (0.5 g, 3.12 mmol, Eq: 1.00) in dichloromethane (31.5 ml) at 0° C. were added tert-butyl 2-oxoethylcarbamate (628 mg, 3.75 mmol, Eq: 1.2) and AcOH (187 mg, 179 µl, 3.12 mmol, Eq: 1.00). The solution was stirred at 0° C. for 0.5 h. Then sodium triacetoxyborohydride (992 mg, 4.68 mmol) was added, and the solution was stirred at 23° C. for 6 h. The mixture was diluted with water (20 ml), the organic layer was separated and the aqueous layer was extracted with dichloromethane. The organic layers were washed with brine, dried over $MgSO_4$ and evaporated. The crude product (1.25 g) was purified by flash chromatography to give the title compound (0.92 g, 97%). MS: 304.2 $(M+H)^+$.

Step 2: 1-(4-(Oxazol-5-yl)phenyl)imidazolidin-2-one

To a solution of potassium tert-butoxide (681 mg, 6.07 mmol) in THF (25.5 ml) at 0° C. was added a solution of tert-butyl 2-(4-(oxazol-5-yl)phenylamino)ethylcarbamate (0.92 g, 3.03 mmol) in THF (25.5 ml), and the resulting solution was stirred at 23° C. for 2 h. The mixture was quenched with 100 ml sat. aqueous $NH_4Cl$ sol. and extracted with EtOAc. The organic phase was washed with brine, dried over $MgSO_4$ and evaporated. The crude product (0.65 g) was triturated with 3 ml AcOEt and 10 ml heptane. After ½ h the mixture was filtered, washed with heptane and dried at HV to give the title compound (560 mg, 81%).

Step 3: 1-[(3-Methoxyphenyl)methyl]-3-[4-(1,3-oxazol-5-yl)phenyl]imidazolidin-2-one To a suspension of sodium hydride (21.0 mg, 525 µmol) in DMF (1.35 ml) at 0° C. was added a solution of 1-(4-(oxazol-5-yl)phenyl)imidazolidin-2-one (80.2 mg, 0.35 mmol) in DMF (3.37 ml), and the resulting mixture was stirred at 0° C. for 0.5 h. Then 1-(bromomethyl)-3-methoxybenzene (106 mg, 73.5 µl, 525 µmol) was added to the mixture. The solution was stirred for further 19 h at 23° C. The mixture was diluted with 20 ml water and extracted with EtOAc. The organic layer was washed with brine, dried over $MgSO_4$ and evaporated. The crude material (1.31 g) was purified by column chromatography (silica gel, 20 g, heptan/AcOEt 0-50%). The product (0.06 g) was crystallised with 2 ml dichloromethane and 15 ml heptan. After ½ h the mixture was filtered, washed with heptane and dried at HV to give 24 mg (20%) of the title compound. MS: 350.2 $(M+H)^+$.

Example 60

3-(3-Fluorophenyl)-1-[4-(1,3-oxazol-5-yl)phenyl]pyrrolidin-2-one

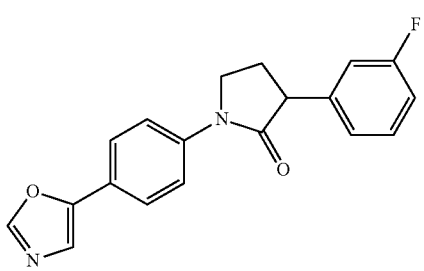 [SMILES: O=C1C(c2cccc(F)c2)CCN1c1ccc(-c2cnco2)cc1]

The title compound was prepared in analogy to Example 3, using 3-fluorophenylacetic acid in step 1, and 4-oxazol-5-ylaniline in step 2. MS: 323.2 $(M+H)^+$.

Example 61

3-(3-Fluorophenyl)-1-[3-methoxy-4-(1,3-oxazol-5-yl)phenyl]pyrrolidin-2-one

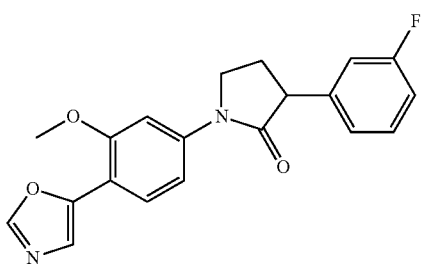 [SMILES: COc1cc(N2CCC(c3cccc(F)c3)C2=O)ccc1-c1cnco1]

The title compound was prepared in analogy to Example 3, using 3-fluorophenylacetic acid in step 1. MS: 353.2 $(M+H)^+$.

Example 62

1-[3-Methoxy-4-(1H-pyrazol-4-yl)phenyl]-3-(4-pyridylmethyl)imidazolidin-2-one

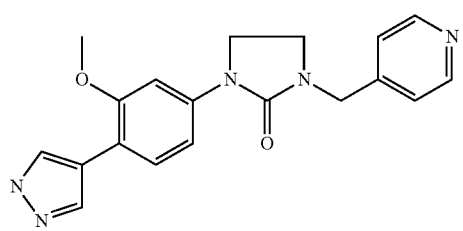 [SMILES: COc1cc(N2CCN(Cc3ccncc3)C2=O)ccc1-c1cn[nH]c1]

The title compound was prepared in analogy to Example 5, using tert-butyl N-(2-oxoethyl)carbamate in Step 1, and 4-(bromomethyl)pyridine in Step 3. LC-MS: 350 (M+H)⁺.

Example 63

1-[3-Methoxy-4-(1H-pyrazol-4-yl)phenyl]-3-(2-pyridylmethyl)imidazolidin-2-one

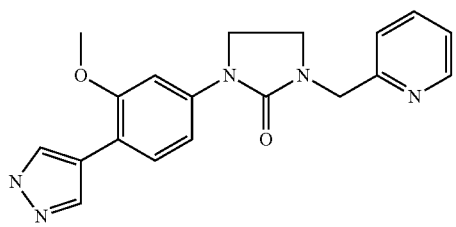 [SMILES: COc1cc(N2CCN(Cc3ccccn3)C2=O)ccc1-c1cn[nH]c1]

The title compound was prepared in analogy to Example 5, using tert-butyl N-(2-oxoethyl)carbamate in Step 1, and 2-(bromomethyl)pyridine in Step 3. LC-MS: 350 (M+H)⁺.

Example 64

1-[3-Methoxy-4-(1H-pyrazol-4-yl)phenyl]-3-(2-phenylpropyl)imidazolidin-2-one

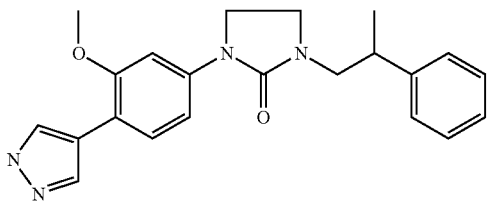 [SMILES: COc1cc(N2CCN(CC(C)c3ccccc3)C2=O)ccc1-c1cn[nH]c1]

The title compound was prepared in analogy to Example 5, using tert-butyl N-(2-oxoethyl)carbamate in Step 1, and (2-bromo-1-methyl-ethyl)benzene in Step 3. LC-MS: 377 (M+H)⁺.

Example 65

1-[3-Methoxy-4-(4-pyridyl)phenyl]-3-(m-tolylmethyl)imidazolidin-2-one

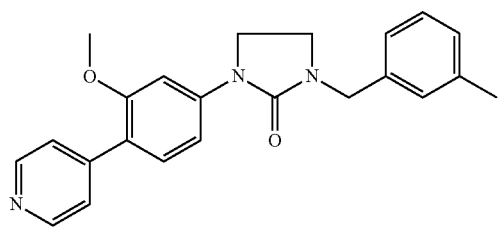 [SMILES: COc1cc(N2CCN(Cc3cccc(C)c3)C2=O)ccc1-c1ccncc1]

The title compound was prepared in analogy to Example 5, using tert-butyl N-(2-oxoethyl)carbamate in Step 1, 1-(bromomethyl)-3-methyl-benzene in Step 3, and pyridin-4-ylboronic acid in Step 4. LC-MS: 374 (M+H)⁺.

Example 66

1-[3-Methoxy-4-(4-pyridyl)phenyl]-3-(3-pyridylmethyl)imidazolidin-2-one

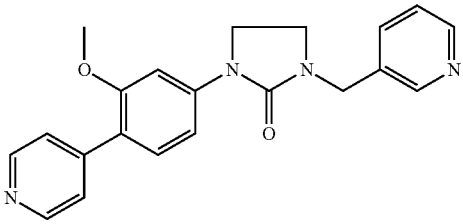 [SMILES: COc1cc(N2CCN(Cc3cccnc3)C2=O)ccc1-c1ccncc1]

The title compound was prepared in analogy to Example 5, using tert-butyl N-(2-oxoethyl)carbamate in Step 1, 3-(bromomethyl)pyridine in Step 3, and pyridin-4-ylboronic acid in Step 4. LC-MS: 361 (M+H)⁺.

Example 67

1-[3-Methoxy-4-(1,3-oxazol-5-yl)phenyl]-3-[(2-methoxyphenyl)methyl]imidazolidin-2-one

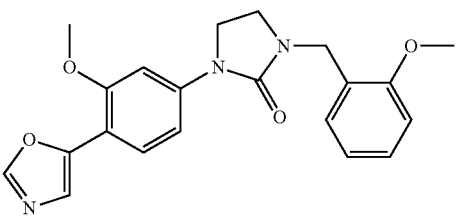 [SMILES: COc1ccccc1CN1CCN(c2ccc(-c3cnco3)c(OC)c2)C1=O]

The title compound was prepared in analogy to Example 59, using 3-methoxy-4-(oxazol-5-yl)aniline in step 1 and 1-(chloromethyl)-2-methoxybenzene in step 3. MS: 380.2 (M+H)⁺.

Example 68

1-[3-Methoxy-4-(1,3-oxazol-5-yl)phenyl]-3-[(3-methoxyphenyl)methyl]imidazolidin-2-one

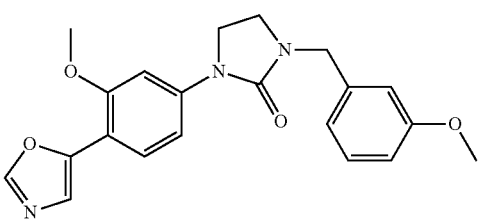 [SMILES: COc1cccc(CN2CCN(c3ccc(-c4cnco4)c(OC)c3)C2=O)c1]

The title compound was prepared in analogy to Example 59, using 3-methoxy-4-(oxazol-5-yl)aniline in step 1 and 1-(bromomethyl)-3-methoxybenzene in step 3. MS: 380.2 (M+H)⁺.

Example 69

1-[(2-Chlorophenyl)methyl]-3-[3-methoxy-4-(1,3-oxazol-5-yl)phenyl]imidazolidin-2-one

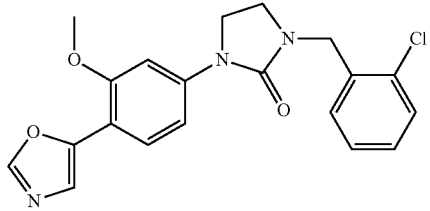 [SMILES: COc1cc(N2CCN(Cc3ccccc3Cl)C2=O)ccc1-c1cnco1]

The title compound was prepared in analogy to Example 59, using 3-methoxy-4-(oxazol-5-yl)aniline in step 1 and 1-(bromomethyl)-3-chlorobenzene in step 3. MS: 384.2 (M+H)$^+$.

Example 70

3-(3-Methoxyphenyl)-1-(3-methoxy-4-pyridin-4-ylphenyl)pyrrolidin-2-one

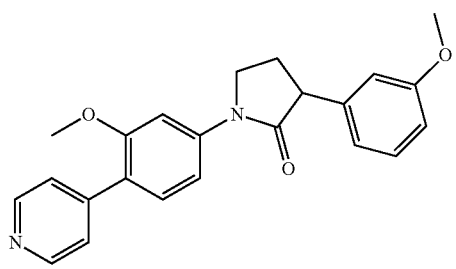 [SMILES: COc1cccc(C2CCN(c3ccc(-c4ccncc4)c(OC)c3)C2=O)c1]

The title compound was prepared in analogy to Example 12, using 3-methylphenyl acetic acid in step 1, and pyridin-4-ylboronic acid in step 6. LC-MS: 375.3 (M+H)$^+$.

Example 71

3-(3-Methoxyphenyl)-1-(4-pyridin-4-ylphenyl)pyrrolidin-2-one

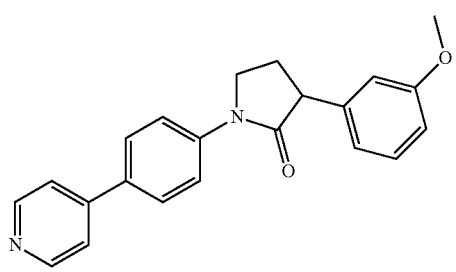 [SMILES: COc1cccc(C2CCN(c3ccc(-c4ccncc4)cc3)C2=O)c1]

The title compound was prepared in analogy to Example 12, using 3-methylphenyl acetic acid in step 1, 4-bromoaniline in Step 2, and pyridin-4-ylboronic acid in step 6. LC-MS: 345.3 (M+H)$^+$.

Example 72

1-[(3-Fluorophenyl)methyl]-3-[4-(1,3-oxazol-5-yl)phenyl]imidazolidin-2-one

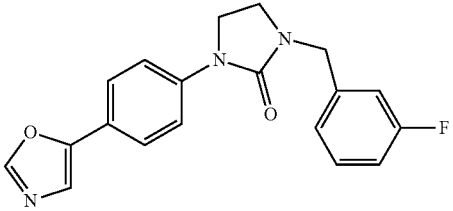 [SMILES: O=C1N(Cc2cccc(F)c2)CCN1c1ccc(-c2cnco2)cc1]

The title compound was prepared in analogy to Example 59, using 1-(bromomethyl)-3-fluorobenzene in step 3. MS: 338.2 (M+H)$^+$.

Example 73

1-[(2-Fluorophenyl)methyl]-3-[4-(1,3-oxazol-5-yl)phenyl]imidazolidin-2-one

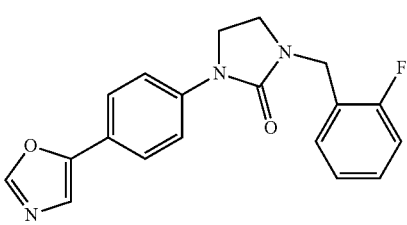 [SMILES: O=C1N(Cc2ccccc2F)CCN1c1ccc(-c2cnco2)cc1]

The title compound was prepared in analogy to Example 59, using 1-(bromomethyl)-2-fluorobenzene in step 3. MS: 338.2 (M+H)$^+$.

Example 74

1-[(2-Fluorophenyl)methyl]-3-[3-methoxy-4-(1,3-oxazol-5-yl)phenyl]imidazolidin-2-one

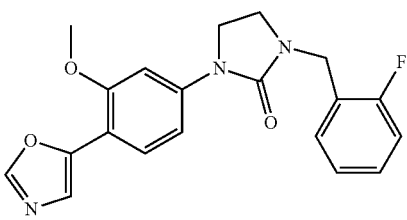 [SMILES: COc1cc(N2CCN(Cc3ccccc3F)C2=O)ccc1-c1cnco1]

The title compound was prepared in analogy to Example 59, using 3-methoxy-4-(oxazol-5-yl)aniline in step 1 and 1-(bromomethyl)-2-fluorobenzene in step 3. MS: 368.2 (M+H)$^+$.

Example 75

1-[(3-Fluorophenyl)methyl]-3-[3-methoxy-4-(1,3-oxazol-5-yl)phenyl]imidazolidin-2-one

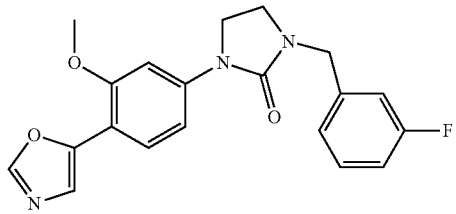 [SMILES: COc1cc(N2CCN(Cc3cccc(F)c3)C2=O)ccc1-c1cnco1]

The title compound was prepared in analogy to Example 59, using 3-methoxy-4-(oxazol-5-yl)aniline in step 1 and 1-(bromomethyl)-3-fluorobenzene in step 3. MS: 368.2 (M+H)$^+$.

We claim:

1. A compound of formula I

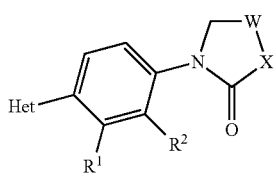

I wherein
Het is oxazole-5-yl, pyridin-4-yl, or pyrazol-4-yl;
$R^1$ and $R^2$ are each independently hydrogen, lower alkyl, lower alkoxy, or halogen;
W is —CH$_2$— or —CH$_2$CH$_2$—;
X is CR$^3$R$^4$ or NR$^5$;
$R^3$ is hydrogen or lower alkyl;
$R^4$ is —(CH$_2$)$_n$-phenyl, optionally substituted by halogen, lower alkoxy, lower alkyl substituted by halogen, lower alkoxy substituted by halogen or lower alkyl;
$R^5$ is CHR-phenyl or CH$_2$CHR-phenyl, optionally substituted by halogen, lower alkoxy, lower alkyl substituted by halogen, lower alkoxy substituted by halogen or lower alkyl, or is CHR-pyridin-2-yl, CHR-pyridin-3-yl or CHR-pyridin-4-yl;
R is hydrogen or lower alkyl;
n is 0 or 1;
or a pharmaceutically acceptable acid addition salt, a racemic mixture or its corresponding enantiomer and/or optical isomer thereof;
with the proviso that when X is CR$^3$R$^4$, Het is pyridine-4-yl or pyrazol-4-yl.

2. The compound of formula Ia according to claim 1,

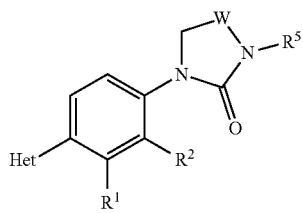

Ia wherein
Het is oxazole-5-yl, pyridin-4-yl, or pyrazol-4-yl;
$R^1$ and $R^2$ are each independently hydrogen, lower alkyl, lower alkoxy, or halogen;
W is —CH$_2$— or —CH$_2$CH$_2$—;
$R^5$ is CHR-phenyl or CH$_2$CHR-phenyl, optionally substituted by halogen, lower alkoxy, lower alkyl substituted by halogen, lower alkoxy substituted by halogen or lower alkyl, or is CHR-pyridin-3-yl or CHR-pyridin-4-yl;
R is hydrogen or lower alkyl;
or a pharmaceutically acceptable acid addition salt, a racemic mixture or its corresponding enantiomer and/or optical isomer thereof.

3. The compound of formula Ia-1 according to claim 2,

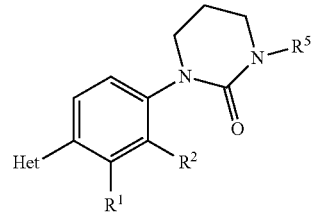

Ia-1 wherein
Het is oxazole-5-yl, pyridine-4-yl, or pyrazol-4-yl;
$R^1$ and $R^2$ are each independently hydrogen, lower alkyl, lower alkoxy, or halogen;
$R^5$ is CHR-phenyl or CH$_2$CHR-phenyl, optionally substituted by halogen, lower alkoxy, lower alkyl substituted by halogen, lower alkoxy substituted by halogen or lower alkyl, or is CHR-pyridin-3-yl or CHR-pyridin-4-yl;
R is hydrogen or lower alkyl;
or a pharmaceutically acceptable acid addition salt, a racemic mixture or its corresponding enantiomer and/or optical isomer thereof.

4. The compound of claim 3 which compound is selected from the group consisting of:
1-benzyl-3-[3-methoxy-4-(1H-pyrazol-4-yl)phenyl]hexahydropyrimidin-2-one;
1-[(2-chlorophenyl)methyl]-3-[3-methoxy-4-(1H-pyrazol-4-yl)phenyl]hexahydropyrimidin-2-one; and,
1-[(3-methoxyphenyl)methyl]-3-[3-methoxy-4-(1H-pyrazol-4-yl)phenyl]hexahydropyrimidin-2-one; or,
a pharmaceutically acceptable salt thereof.

5. The compound of formula Ia-2 according to claim 2,

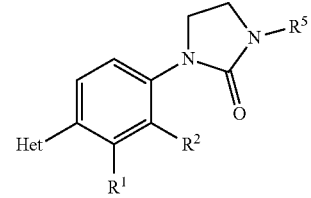

Ia-2 wherein
Het is oxazole-5-yl, pyridin-4-yl, or pyrazol-4-yl;
$R^1$ and $R^2$ are each independently hydrogen, lower alkyl, lower alkoxy, or halogen;

R⁵ is CHR-phenyl or CH₂CHR-phenyl, optionally substituted by halogen, lower alkoxy, lower alkyl substituted by halogen, lower alkoxy substituted by halogen or lower alkyl, or is CHR-pyridin-3-yl or CHR-pyridin-4-yl;

R is hydrogen or lower alkyl;

or a pharmaceutically acceptable acid addition salt, a racemic mixture or its corresponding enantiomer and/or optical isomer thereof.

6. The compound of claim 5 which compound is selected from the group consisting of:
1-benzyl-3-(4-(pyridin-4-yl)phenyl)imidazolidin-2-one;
1-benzyl-3-[3-methoxy-4-(1H-pyrazol-4-yl)phenyl]imidazolidin-2-one;
1-[(2-chlorophenyl)methyl]-3-[3-methoxy-4-(1H-pyrazol-4-yl)phenyl]imidazolidin-2-one;
1-[(3-methoxyphenyl)methyl]-3-[3-methoxy-4-(1H-pyrazol-4-yl)phenyl]imidazolidin-2-one;
1-[(3-chlorophenyl)methyl]-3-[3-methoxy-4-(1H-pyrazol-4-yl)phenyl]imidazolidin-2-one;
1-[(3-fluorophenyl)methyl]-3-[3-methoxy-4-(1H-pyrazol-4-yl)phenyl]imidazolidin-2-one;
1-[3-methoxy-4-(1H-pyrazol-4-yl)phenyl]-3-[[3-(trifluoromethyl)phenyl]methyl]imidazolidin-2-one;
1-[3-methoxy-4-(1H-pyrazol-4-yl)phenyl]-3-[[3-(trifluoromethoxy)phenyl]methyl]imidazolidin-2-one;
1-[(3-ethoxyphenyl)methyl]-3-[3-methoxy-4-(1H-pyrazol-4-yl)phenyl]imidazolidin-2-one;
1-[(3-methoxyphenyl)methyl]-3-[4-(1H-pyrazol-4-yl)phenyl]imidazolidin-2-one;
1-[(3-methoxyphenyl)methyl]-3-[3-methyl-4-(1H-pyrazol-4-yl)phenyl]imidazolidin-2-one;
1-[3-chloro-4-(1H-pyrazol-4-yl)phenyl]-3-[(3-methoxyphenyl)methyl]imidazolidin-2-one;
1-[2-fluoro-4-(1H-pyrazol-4-yl)phenyl]-3-[(3-methoxyphenyl)methyl]imidazolidin-2-one;
1-[3-fluoro-4-(1H-pyrazol-4-yl)phenyl]-3-[(3-methoxyphenyl)methyl]imidazolidin-2-one;
1-[3-ethoxy-4-(1H-pyrazol-4-yl)phenyl]-3-[(3-methoxyphenyl)methyl]imidazolidin-2-one;
1-[(2-fluorophenyl)methyl]-3-[3-methoxy-4-(1H-pyrazol-4-yl)phenyl]imidazolidin-2-one;
1-[3-methoxy-4-(1H-pyrazol-4-yl)phenyl]-3-(o-tolylmethyl)imidazolidin-2-one;
1-[3-methoxy-4-(1H-pyrazol-4-yl)phenyl]-3-(m-tolylmethyl)imidazolidin-2-one;
1-[(3-methoxyphenyl)methyl]-3-[2-methoxy-4-(1H-pyrazol-4-yl)phenyl]imidazolidin-2-one;
1-[(2-methoxyphenyl)methyl]-3-[3-methoxy-4-(1H-pyrazol-4-yl)phenyl]imidazolidin-2-one;
1-[3-methoxy-4-(1H-pyrazol-4-yl)phenyl]-3-(2-phenylethyl)imidazolidin-2-one;
1-[2-(2-methoxyphenyl)ethyl]-3-[3-methoxy-4-(1H-pyrazol-4-yl)phenyl]imidazolidin-2-one;
1-[2-(2-chlorophenyl)ethyl]-3-[3-methoxy-4-(1H-pyrazol-4-yl)phenyl]imidazolidin-2-one;
1-[2-chloro-4-(1H-pyrazol-4-yl)phenyl]-3-[(3-methoxyphenyl)methyl]imidazolidin-2-one;
1-[(4-fluorophenyl)methyl]-3-[3-methoxy-4-(1H-pyrazol-4-yl)phenyl]imidazolidin-2-one;
1-[3-methoxy-4-(1H-pyrazol-4-yl)phenyl]-3-(3-pyridylmethyl)imidazolidin-2-one;
1-[2-(3-chlorophenyl)ethyl]-3-[3-methoxy-4-(1H-pyrazol-4-yl)phenyl]imidazolidin-2-one;
1-[2-(4-chlorophenyl)ethyl]-3-[3-methoxy-4-(1H-pyrazol-4-yl)phenyl]imidazolidin-2-one;
1-[3-methoxy-4-(1H-pyrazol-4-yl)phenyl]-3-(1-phenylpropyl)imidazolidin-2-one;
1-[3-methoxy-4-(4-pyridyl)phenyl]-3-[[2-(trifluoromethyl)phenyl]methyl]imidazolidin-2-one;
1-[3-methoxy-4-(4-pyridyl)phenyl]-3-(4-pyridylmethyl)imidazolidin-2-one;
1-[(3-methoxyphenyl)methyl]-3-[4-(1,3-oxazol-5-yl)phenyl]imidazolidin-2-one;
1-[3-methoxy-4-(1H-pyrazol-4-yl)phenyl]-3-(4-pyridylmethyl)imidazolidin-2-one;
1-[3-methoxy-4-(1H-pyrazol-4-yl)phenyl]-3-(2-pyridylmethyl)imidazolidin-2-one;
1-[3-methoxy-4-(1H-pyrazol-4-yl)phenyl]-3-(2-phenylpropyl)imidazolidin-2-one;
1-[3-methoxy-4-(4-pyridyl)phenyl]-3-(m-tolylmethyl)imidazolidin-2-one;
1-[3-methoxy-4-(4-pyridyl)phenyl]-3-(3-pyridylmethyl)imidazolidin-2-one;
1-[3-methoxy-4-(1,3-oxazol-5-yl)phenyl]-3-[(2-methoxyphenyl)methyl]imidazolidin-2-one;
1-[3-methoxy-4-(1,3-oxazol-5-yl)phenyl]-3-[(3-methoxyphenyl)methyl]imidazolidin-2-one;
1-[(2-chlorophenyl)methyl]-3-[3-methoxy-4-(1,3-oxazol-5-yl)phenyl]imidazolidin-2-one;
1-[(3-fluorophenyl)methyl]-3-[4-(1,3-oxazol-5-yl)phenyl]imidazolidin-2-one;
1-[(2-fluorophenyl)methyl]-3-[4-(1,3-oxazol-5-yl)phenyl]imidazolidin-2-one;
1-[(2-fluorophenyl)methyl]-3-[3-methoxy-4-(1,3-oxazol-5-yl)phenyl]imidazolidin-2-one; and,
1-[(3-fluorophenyl)methyl]-3-[3-methoxy-4-(1,3-oxazol-5-yl)phenyl]imidazolidin-2-one; or,
a pharmaceutically acceptable salt thereof.

7. The compound of formula Ib according to claim 1,

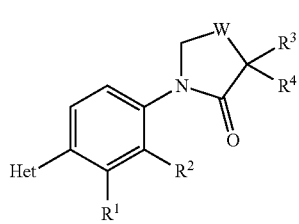

wherein

Het is pyridin-4-yl or pyrazol-4-yl;

R¹ and R² are each independently hydrogen, lower alkyl, lower alkoxy, or halogen;

W is —CH₂— or —CH₂CH₂—;

R³ is hydrogen or lower alkyl;

R⁴ is —(CH₂)$_n$-phenyl, optionally substituted by halogen, lower alkoxy, lower alkyl substituted by halogen, lower alkoxy substituted by halogen or lower alkyl;

n is 0 or 1;

or a pharmaceutically acceptable acid addition salt, a racemic mixture or its corresponding enantiomer and/or optical isomer thereof.

8. The compound of formula Ib-1 according to claim 7

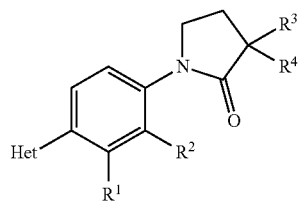

wherein
Het is pyridin-4-yl or pyrazol-4-yl;
$R^1/R^2$ are each independently hydrogen, lower alkyl, lower alkoxy, or halogen;
$R^3$ is hydrogen or lower alkyl;
$R^4$ is —$(CH_2)_n$-phenyl, optionally substituted by halogen, lower alkoxy, lower alkyl substituted by halogen, lower alkoxy substituted by halogen or lower alkyl;
n is 0 or 1;
or a pharmaceutically acceptable acid addition salt, a racemic mixture or its corresponding enantiomer and/or optical isomer thereof.

9. The compound of claim 8 which compound is selected from the group consisting of:
1-[3-methoxy-4-(1H-pyrazol-4-yl)phenyl]-3-phenyl-pyrrolidin-2-one;
3-phenyl-1-[4-(1H-pyrazol-4-yl)phenyl]pyrrolidin-2-one;
3-(3-methoxyphenyl)-1-[4-(1H-pyrazol-4-yl)phenyl]pyrrolidin-2-one;
3-(4-chlorophenyl)-1-[4-(1H-pyrazol-4-yl)phenyl]pyrrolidin-2-one;
3-(4-fluorophenyl)-1-[4-(1H-pyrazol-4-yl)phenyl]pyrrolidin-2-one;
3-(3-chlorophenyl)-1-[4-(1H-pyrazol-4-yl)phenyl]pyrrolidin-2-one;
3-benzyl-1-(3-methoxy-4-(1H-pyrazol-4-yl)phenyl)pyrrolidin-2-one;
1-(3-methoxy-4-(1H-pyrazol-4-yl)phenyl)-3-(3-methoxyphenyl)pyrrolidin-2-one;
3-(3-chlorophenyl)-1-(3-methoxy-4-(1H-pyrazol-4-yl)phenyl)pyrrolidin-2-one;
3-(3-fluorophenyl)-1-(3-methoxy-4-(1H-pyrazol-4-yl)phenyl)pyrrolidin-2-one;
3-[(3-chlorophenyl)methyl]-1-[3-methoxy-4-(1H-pyrazol-4-yl)phenyl]pyrrolidin-2-one;
3-[(2-chlorophenyl)methyl]-1-[3-methoxy-4-(1H-pyrazol-4-yl)phenyl]pyrrolidin-2-one;
3-[(3-methoxyphenyl)methyl]-1-[3-methoxy-4-(1H-pyrazol-4-yl)phenyl]pyrrolidin-2-one;
3-(3-methoxyphenyl)-1-(3-methoxy-4-pyridin-4-ylphenyl)pyrrolidin-2-one; and,
3-(3-methoxyphenyl)-1-(4-pyridin-4-ylphenyl)pyrrolidin-2-one; or,
a pharmaceutically acceptable salt thereof.

10. A pharmaceutical composition comprising a compound of claim 1 and at least one pharmaceutically acceptable carrier, diluent or excipient.

* * * * *